(12) United States Patent
Yoshinaga et al.

(10) Patent No.: US 7,732,544 B2
(45) Date of Patent: Jun. 8, 2010

(54) TITANIUM COMPOUND AND PROCESS FOR PRODUCING OPTICALLY ACTIVE CYANOHYDRINS

(75) Inventors: Kazuhiko Yoshinaga, Jurong Island (SG); Takushi Nagata, Jurong Island (SG); Satoru Miyazoe, Ichihara-shi (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 391 days.

(21) Appl. No.: 11/665,346

(22) PCT Filed: Oct. 6, 2005

(86) PCT No.: PCT/JP2005/018527

§ 371 (c)(1),
(2), (4) Date: Apr. 13, 2007

(87) PCT Pub. No.: WO2006/041000

PCT Pub. Date: Apr. 20, 2006

(65) Prior Publication Data

US 2007/0265463 A1 Nov. 15, 2007

(30) Foreign Application Priority Data

Oct. 15, 2004 (JP) ............................. 2004-301114

(51) Int. Cl.
*C08F 2/22* (2006.01)
(52) U.S. Cl. .................... 526/201; 524/923; 556/30; 556/33; 558/423
(58) Field of Classification Search .................. None
See application file for complete search history.

(56) References Cited

FOREIGN PATENT DOCUMENTS

| JP | 5-112518 A | 5/1993 |
|---|---|---|
| JP | 2000-191677 A | 7/2000 |
| JP | 2002-255985 A | 9/2002 |
| WO | WO 02/10095 A2 | 2/2002 |
| WO | WO 02/10095 A3 | 2/2002 |

OTHER PUBLICATIONS

Gama et al. "Steric effects in the design of chiral Schiff base-titanium complexes: new catalysts for asymmetric trimethylsilylcyanation of aldehydes" Tetrahedron: Asymmetry, 2002, vol. 13, pp. 149-154.*
Brozda, et al. Tetrandron: Asymmetry, vol. 16, pp. 953-958 (2005).*
Gama, et al. Tetrahdron: Asymmetry, vol. 13, pp. 149-154 (2002).*
Bensari, et al. Org. Lett., vol. 3(24), pp. 3863-3865 (2001).*
Hayashi, et al. J. Chem. Soc., Chem. Commun., vol. 3, pp. 341-342 (1994).*
Angeles Gama et al., "Steric effects in the design of chiral Schiff base-titanium complexes: new catalysts for asymmetric trimethylsilylcyanation of aldehydes", Tetrahedron:Asymmetry, 2002, pp. 149-154, No. 13, ISSN:0957-4166, XP-002468255, Elsevier Science Ltd.
Lucía Z. Flores-Lopéz et al., "Structure/Enantioselectivity Study of the Asymmetric Addition of Trimethylsilylcyanide to Benzaldehyde Catalyzed by Ti(IV)-Schiff Base Complexes", Organometallics, 2000, pp. 2153-2160, No. 19, ISSN:0276-7333, XP-002468256, American Chemical Society.
Xiang-Ge Zhou et al., "Titanium and ruthenium binaphthyl Schiff base complexes as catalysts for asymmetric trimethylsilylcyanation of aldehydes", Journal of the Chemical Society, Dalton Transactions, Chemical Society, 1999, pp. 3303-3309, No. 18, ISSN:1472-7773, XP-002201075, The Royal Society of Chemistry.
V.W. Day et al., "Solution Structure Elucidation of Early-Transition-Metal Polyoxoalkoxides Using $^{17}O$ Nuclear Magnetic Resonance Spectroscopy", Journal of the American Chemical Society, 1991, pp. 8190-8192, vol. 113, No. 21, ISSN:0002-7863, XP-002468257, American Chemical Society.
Yuri N. Belokon et al.; "The Asymmetric Addition of Trimethylsilyl Cyanide to Aldehydes Catalyzed by Chiral (Salen)Titanium Complexes"; J. Am. Chem. Soc.; 1999; pp. 3968-3973; vol. 121; American Chemical Society.

(Continued)

*Primary Examiner*—Kamal A Saeed
*Assistant Examiner*—Michael Barker
(74) *Attorney, Agent, or Firm*—Buchanan Ingersoll & Rooney PC

(57) ABSTRACT

The present invention relates to a titanium compound produced from a reaction mixture of a titanium tetraalkoxide compound with water and an optically active ligand represented by the following general formula (1), or a titanium oxoalkoxide compound and an optically active ligand represented by the following general formula (1),

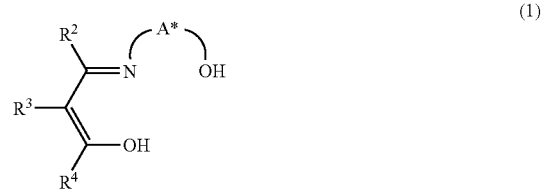

(1)

wherein, in the formula, $R^2$, $R^3$ and $R^4$ independently represent a hydrogen atom, an alkyl group or the like, and $A^*$ represents a hydrocarbon-containing group with three or more carbon atoms having an asymmetric carbon atom or axial asymmetry. The invention further relates to a process for producing optically active cyanohydrins which is characterized by reacting a carbonyl compound with a cyanating agent in the presence of such a titanium compound.

15 Claims, 2 Drawing Sheets

OTHER PUBLICATIONS

Masahiko Hayashi et al.; "Asymmetric Carbon-Carbon Bond Forming Reactions Catalyzed by Chiral Schiff Base-Titanium Alkoxide Complexes"; Tetrahedron; 1994; pp. 4385-4398; vol. 50, No. 14; BPC-AUP Aberdeen Ltd., Great Britain.

Yaozhong Jiang et al.; "Asymmetric Synthesis XXII:Asymmetric Catalytic Trimethylsilylcyanation of Benzaldehyde by Novel (Ti(IV)-Chiral Schiff Base Complexes"; Tetrahedron:Asymmetry; Feb. 1995; pp. 405-408; vol. 6, No. 2; Elsevier Science, Ltd., Great Britain.

* cited by examiner

¹H NMR Spectrum Chart a) Ti(OnBu)₄; prior to reaction with water b) Reaction mixture of Ti(OnBu)₄ with water
   (Partial hydrolysate prepared in Preparation Example 7)

TITANIUM COMPOUND AND PROCESS FOR PRODUCING OPTICALLY ACTIVE CYANOHYDRINS

TECHNICAL FIELD

The present invention relates to a titanium compound and a process for producing optically active cyanohydrins according to the asymmetric cyanation reaction of aldehyde or ketone using such a titanium compound. The optically active cyanohydrins are useful as an intermediate in the synthesis of pharmaceutical and agricultural chemicals.

BACKGROUND ART

There has already been generally known that asymmetric synthetic reactions can be carried out by using a metal complex prepared from an alkoxide or halide of metal such as titanium, aluminum or the like and an optically active compound as a catalyst. Of these, the reaction for synthesizing optically active cyanohydrins according to the asymmetric cyanation of aldehyde is particularly important as an enantioselective reaction increasing the number of carbon atoms, and various cases thereof as shown below have been reported.

(1) a method using a titanium complex with a chiral Schiff base prepared from optically active β-aminoalcohols and salicylaldehyde as a catalyst (Patent Document 1), (2) a method using a titanium complex or a vanadium complex prepared from an optically active, tetradentate ligand called a salen type as a catalyst (Non-patent Document 1 and Patent Document 2), and (3) a method using an aluminum complex prepared from an optically active binaphthyl compound as a catalyst (Patent Document 3).

However, the method (1) requires very low reaction temperature, around −78 degree C., and 10 to 20 mol % of the catalyst to obtain corresponding cyanohydrins with high enantioselectivities. In addition, the catalyst gives good enantioselectivities for very limited aldehydes. Regarding the method (2), enantioselectivity of the catalyst is not sufficient for aliphatic aldehydes in particular although the above mentioned problems are improved. The catalyst in the method (3) shows very high enantioselectivity for asymmetric cyanation of various aliphatic and aromatic aldehydes therefore the catalyst is regarded as a versatile catalyst. However, the catalyst is hardly adequate from the practical point of view because cyanating agent must be added for a long period of time, long reaction time, 36 to 70 hours, is required to complete the reaction and low reaction temperature, −40 degree C., is necessary. Reducing the amount of catalyst also remains as a problem to be solved.

On the other hand, in the asymmetric cyanation reaction of ketone, asymmetric catalysts exhibiting high enantioselectivity have hardly been known. One of a few examples include a method using a titanium complex or a rare earth metal complex prepared from an optically active, tridentate ligand derived from glucose as a catalyst, so there has been reported that cyanohydrins with a high optical purity are obtained from various substrates (Patent Document 4).

However, there have not been known asymmetric cyanation catalysts which can be applied to a wide range of substrates, achieve high yield and high enantioselectivity, obtain a desired product within a short period of time, and does not require facilities for the reaction at a low temperature.

Furthermore, there has also been demanded development of asymmetric cyanation catalysts combining industrially desired conditions such that they can be produced with ease and have high activity, and the amount thereof is suppressed low.

Patent Document 1: Japanese Patent Laid-open No. 1993-112518
Patent Document 2: WO02/10095
Patent Document 3: Japanese Patent Laid-open No. 2000-191677
Patent Document 4: Japanese Patent Laid-open No. 2002-255985
Non-patent Document 1: J. Am. Chem. Soc., Vol. 121, p. 3968 (1999)

DISCLOSURE OF THE INVENTION

An object of the present invention is to provide a titanium catalyst which is useful in the asymmetric synthesis reaction.

Further, another object of the present invention is to provide a process for producing optically active cyanohydrins which are industrially favorable, can carry out the reaction under the practical reaction conditions by using the titanium compound and can be applied to a wide range of substrates.

In order to solve the above objects, the present inventors have conducted an extensive study, and as a result, have found that a novel titanium compound produced from a titanium tetraalkoxide compound, water and an optically active, tridentate ligand, or a novel titanium compound produced from a titanium oxoalkoxide compound and an optically active, tridentate ligand is effective as a catalyst for the asymmetric synthesis reaction and particularly a catalyst for the asymmetric cyanation reaction of aldehyde or unsymmetrical ketone.

That is, the present invention includes the following inventions:

(1) a titanium compound produced from a reaction mixture of a titanium tetraalkoxide compound with water and an optically active ligand represented by the general formula (b), or a titanium oxoalkoxide compound represented by the general formula (a) and an optically active ligand represented by the general formula (b),

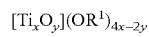

$$[Ti_xO_y](OR^1)_{4x-2y} \quad (a)$$

wherein, in the formula, $R^1$ is an alkyl group or an aryl group, each of which may have a substituent; x is an integer of not less than 2; y is an integer of not less than 1; and y/x satisfies $0.1 < y/x \leqq 1.5$,

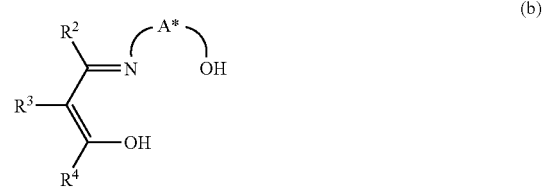

wherein, in the formula, $R^2$, $R^3$ and $R^4$ are independently a hydrogen atom, an alkyl group, an alkenyl group, an aryl group, an aromatic heterocyclic group, an acyl group, an alkoxycarbonyl group or an aryloxycarbonyl group, each of which may have a substituent, two or more of $R^2$, $R^3$ and $R^4$ may be linked together to form a ring, and the ring may have a substituent; and A* represents a hydrocarbon-containing group with three or more carbon atoms having an asymmetric carbon atom or axial asymmetry; and (2) a process for producing optically active cyanohydrins which comprises reacting aldehyde or unsymmetrical ketone with a cyanating agent in the presence of the titanium compound as set forth in the above item (1).

According to the present invention, it is possible to conveniently and efficiently produce optically active cyanohydrins with a high optical purity in a much less amount of a catalyst and within a much shorter period of time, as compared to those produced by using an asymmetric catalyst in the past. These optically active cyanohydrins are useful as an intermediate in the synthesis of physiologically active compounds such as medicines, agricultural chemicals and the like, functional materials, or synthetic raw materials in fine chemicals and the like.

BEST MODE FOR CARRYING OUT THE INVENTION

The present invention will be described in more detail below.

[Titanium Tetraalkoxide Compound]

A titanium tetraalkoxide compound to be a raw material of the titanium compound of the present invention is not particularly limited, but preferable examples thereof include those represented by the general formula (a'), $$Ti(OR^1)_4 \quad (a')$$

$R^1$ in the above general formula (a') is an alkyl group or an aryl group, each of which may have a substituent.

As the alkyl group in $R^1$, preferred is a linear, branched or cyclic alkyl group having not more than 20 carbon atoms.

Examples of the linear alkyl group in $R^1$ include a methyl group, an ethyl group, an n-propyl group, an n-butyl group, an n-pentyl group, an n-hexyl group, an n-heptyl group, an n-octyl group, an n-nonyl group, an n-decyl group and the like.

Examples of the branched alkyl group in $R^1$ include an isopropyl group, an isobutyl group, a sec-butyl group, a tert-butyl group, a 2-pentyl group, a 3-pentyl group, an isopentyl group, a neopentyl group, an amyl group and the like.

Examples of the cyclic alkyl group in $R^1$ include a cyclopropyl group, a cyclobutyl group, a cyclopentyl group, a cyclohexyl group, a cycloheptyl group, a cyclooctyl group and the like.

The aforementioned linear, branched or cyclic alkyl group may have, as a substituent, a halogen atom, an aryl group having not more than 20 carbon atoms, an aromatic heterocyclic group having not more than 20 carbon atoms, a non-aromatic heterocyclic group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the alkyl group having a halogen atom include a chloromethyl group, a 2-chloroethyl group, a trifluoromethyl group, a 2,2,2-trifluoroethyl group, a perfluoroethyl group, a perfluorohexyl group and the like.

Examples of the alkyl group having an aryl group include a substituted or unsubstituted aralkyl group such as a benzyl group, a 4-methoxybenzyl group, a 2-phenylethyl group, a cumyl group, an α-naphthylmethyl and the like.

Examples of the alkyl group having an aromatic heterocyclic group include a 2-pyridylmethyl group, a 2-furfuryl group, a 3-furfuryl group, a 2-thienylmethyl group and the like.

Examples of the alkyl group having a non-aromatic heterocyclic group include a 2-tetrahydrofurfuryl group, a 3-tetrahydrofurfuryl group and the like.

Examples of the alkyl group having an oxygen-containing group include a methoxyethyl group, a phenoxyethyl group and the like.

Examples of the alkyl group having a nitrogen-containing group include a 2-(dimethylamino)ethyl group, a 3-(diphenylamino)propyl group and the like.

Examples of the alkyl group having a silicon-containing group include a 2-(trimethylsiloxy)ethyl group and the like.

As the aryl group in $R^1$, preferred is an aryl group having 6 to 20 carbon atoms. Concrete examples thereof include a phenyl group, a naphthyl group, a biphenyl group, an anthryl group and the like.

The aforementioned aryl group may have, as a substituent, a halogen atom, an alkyl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group and a cyano group.

Examples of the silicon-containing group having not more than 20 carbon atoms include those having not more than 20 carbon atoms such as a silyl group, a silyloxy group and the like.

Examples of the aryl group having a halogen atom include a 4-fluorophenyl group, a pentafluorophenyl group and the like.

Examples of the aryl group having an alkyl group include a tolyl group, a dimethylphenyl group, a 2,4,6-trimethylphenyl group, a 4-isopropylphenyl group, a 2,6-diisopropylphenyl group, a 4-tert-butylphenyl group, a 2,6-di-tert-butylphenyl group and the like.

Examples of the aryl group having an oxygen-containing group include an alkoxy-substituted aryl group such as a 4-methoxyphenyl group, a 3,5-dimethoxyphenyl group, a 3,5-diisopropoxyphenyl group, a 2,4,6-triisopropoxyphenyl group and the like; and an aryloxy-substituted aryl group such as a 2,6-diphenoxyphenyl group and the like.

Examples of the aryl group having a nitrogen-containing group include a 4-(dimethylamino)phenyl group, a 4-nitrophenyl group and the like.

Examples of the aryl group having a silicon-containing group include a 3,5-bis(trimethylsilyl)phenyl group, a 3,5-bis(trimethylsiloxy)phenyl group and the like.

Of these, as $R^1$, particularly preferred is a linear alkyl group having not more than 10 carbon atoms such as a methyl group, an ethyl group, an n-propyl group, an n-butyl group, an n-pentyl group, an n-hexyl group, an n-heptyl group, an n-octyl group, an n-nonyl group, an n-decyl group and the like.

[Titanium Oxoalkoxide Compound Represented by the General Formula (a)]

Further, a titanium oxoalkoxide compound represented by the general formula (a) can also be used for the titanium compound of the present invention.

$$[Ti_xO_y](OR^1)_{4x-2y} \quad (a)$$

In the general formula (a), $R^1$ represents the same as those in the above general formula (a'). Namely, $R^1$ represents the same alkyl group or aryl group as those in the above general formula (a'), each of which may have a substituent. x is an integer of not less than 2, y is an integer of not less than 1, and y/x satisfies $0.1 < y/x \leq 1.5$.

As $R^1$ in the above general formula (a), particularly preferred is a linear alkyl group having not more than 10 such as a methyl group, an ethyl group, an n-propyl group, an n-butyl group, an n-pentyl group, an n-hexyl group, an n-heptyl group, an n-octyl group, an n-nonyl group, an n-decyl group and the like.

There has been known that, by reacting the titanium tetraalkoxide compound represented by the above general formula (a') with water, titanium tetraalkoxide is partially hydrolyzed to give a titanium oxoalkoxide compound represented by the above general formula (a) (for example, Inorg. Chim. Acta, Vol. 229, p. 391 (1995)). Depending on the kind of alkoxide and the amount of water used for the hydrolysis, the values of x and y in the above general formula (a) are varied, but are not necessarily determined only one-sidedly. So, it is considered that various kinds of titanium oxoalkoxide mixtures are obtained. Further, there has been reported that various titanium oxoalkoxide mixtures can be stably isolated to respective substances in some cases (for example, J. Am. Chem. Soc., Vol. 113, p. 8190 (1991)).

As a raw material of the titanium compound of the present invention, a reaction mixture of a titanium tetraalkoxide compound with water may be used as it is, or may be used after a titanium oxoalkoxide compound contained in this reaction mixture is first isolated, prior to use.

In this titanium oxoalkoxide compound, x is preferably not less than 2 to not more than 20. Examples thereof include a titanium alkoxide dimer such as $[Ti_2O](OEt)_6$, $[Ti_2O](O\text{-}n\text{-}Pr)_6$, $[Ti_2O](O\text{-}n\text{-}Bu)_6$ and the like; a titanium alkoxide heptamer such as $[Ti_7O_4](OEt)_{20}$, $[Ti_7O_4](O\text{-}n\text{-}Pr)_{20}$, $[Ti_7O_4](O\text{-}n\text{-}Bu)_{20}$ and the like; a titanium alkoxide octamer such as $[Ti_8O_6](OCH_2Ph)_{20}$ and the like; a titanium alkoxide decamer such as $[Ti_{10}O_8](OEt)_{24}$ and the like; a titanium alkoxide undecamer such as $[Ti_{11}O_{13}](O\text{-}i\text{-}Pr)_{18}$ and the like; a titanium alkoxide dodecamer such as $[Ti_{12}O_{16}](O\text{-}i\text{-}Pr)_{16}$ and the like; a titanium alkoxide hexadecamer such as $[Ti_{16}O_{16}](OEt)_{32}$ and the like; and a titanium alkoxide heptadecamer such as $[Ti_{17}O_{24}](O\text{-}i\text{-}Pr)_{20}$ and the like.

The titanium compound of the present invention is produced from a reaction mixture of a titanium tetraalkoxide compound with water and an optically active ligand represented by the general formula (b) and preferably represented by the general formula (c), or a titanium oxoalkoxide compound represented by the above general formula (a) and an optically active ligand represented by the general formula (b) and preferably represented by the general formula (c),

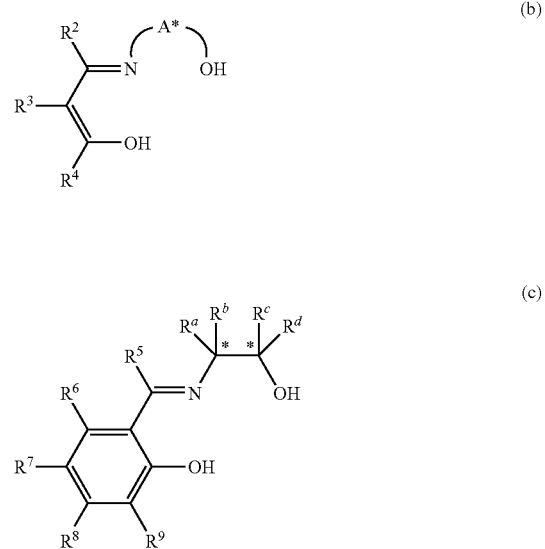

Incidentally, the optically active ligand represented by the above general formula (c) corresponds to those with $R^3$ and $R^4$ in the above general formula (b) bonded together to form a benzene ring, and is included in the concept of the optically active ligand represented by the above general formula (b).

[Optically Active Ligand Represented by the General Formula (b)]

In the above general formula (b), $R^2$, $R^3$ and $R^4$ are independently a hydrogen atom, an alkyl group, an alkenyl group, an aryl group, an aromatic heterocyclic group, an acyl group, an alkoxycarbonyl group or an aryloxycarbonyl group, each of which may have a substituent, two or more of $R^2$, $R^3$ and $R^4$ may be linked together to form a ring, and the ring may have a substituent. Furthermore, A* represents a hydrocarbon-containing group with three or more carbon atoms having an asymmetric carbon atom or axial asymmetry.

As the alkyl group in $R^2$, $R^3$ and $R^4$, preferred is a linear, branched or cyclic alkyl group having not more than 20 carbon atoms, and concrete examples thereof include a methyl group, an ethyl group, an n-propyl group, an isopropyl group, an n-butyl group, an isobutyl group, a sec-butyl group, a tert-butyl group, a cyclopentyl group, a cyclohexyl group and the like.

The aforementioned linear, branched or cyclic alkyl group may have, as a substituent, a halogen atom, an aryl group having not more than 20 carbon atoms, an aromatic heterocyclic group having not more than 20 carbon atoms, a non-aromatic heterocyclic group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the alkyl group having a halogen atom include a chloromethyl group, a 2-chloroethyl group, a trifluoromethyl group, a 2,2,2-trifluoroethyl group, a perfluoroethyl group, a perfluorohexyl group and the like.

Examples of the alkyl group having an aryl group include substituted or unsubstituted aralkyl groups such as a benzyl group, a 4-methoxybenzyl group, a 2-phenylethyl group, a cumyl group, an α-naphthylmethyl group, a diphenylmethyl group, a trityl group and the like.

Examples of the alkyl group having an aromatic heterocyclic group include a 2-pyridylmethyl group, a 2-furfuryl group, a 3-furfuryl group, a 2-thienylmethyl group and the like.

Examples of the alkyl group having a non-aromatic heterocyclic group include a 2-tetrahydrofurfuryl group, a 3-tetrahydrofurfuryl group and the like.

Examples of the alkyl group having an oxygen-containing group include a methoxymethyl group, an isopropoxymethyl group, a tert-butoxymethyl group, a cyclohexyloxymethyl group, an L-menthyloxymethyl group, a D-menthyloxymethyl group, a phenoxymethyl group, a benzyloxymethyl group, a phenoxyethyl group, an acetyloxymethyl group, a 2,4,6-trimethylbenzoyloxymethyl group and the like.

Examples of the alkyl group having a nitrogen-containing group include a 2-(dimethylamino)ethyl group, a 3-(diphenylamino)propyl group and the like.

Examples of the alkyl group having a silicon-containing group include a 2-(trimethylsiloxy)ethyl group and the like.

As the alkenyl group in $R^2$, $R^3$ and $R^4$, preferred is a linear or branched alkenyl group having 2 to 20 carbon atoms, and concrete examples thereof include a vinyl group, an allyl group, an isopropenyl group and the like.

The aforementioned linear or branched alkenyl group may have, as a substituent, a halogen atom such as a fluorine atom, a chlorine atom, a bromine atom, an iodine atom and the like.

Examples of the alkenyl group having a halogen atom include a 2-chlorovinyl group, a 2,2-dichlorovinyl group, a 3-chloroisopropenyl group or the like.

As the aryl group in $R^2$, $R^3$ and $R^4$, preferred is an aryl group having 6 to 20 carbon atoms, and concrete examples thereof include a phenyl group, a naphthyl group, a biphenyl group, an anthryl group and the like.

The aforementioned aryl group may have, as a substituent, a halogen atom, an alkyl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the aryl group having a halogen atom include a 4-fluorophenyl group, a pentafluorophenyl group and the like. Examples of the aryl group having an alkyl group include a tolyl group, a dimethylphenyl group, a 2,4,6-trimethylphenyl group, a 4-isopropylphenyl group, a 2,6-diisopropylphenyl group, a 4-tert-butylphenyl group, a 2,6-di-tert-butylphenyl group and the like.

Examples of the aryl group having an oxygen-containing group include an alkoxy-substituted aryl group such as a 4-methoxyphenyl group, a 3,5-dimethoxyphenyl group, a 3,5-diisopropoxyphenyl group, a 2,4,6-triisopropoxyphenyl group and the like; and an aryloxy-substituted aryl group such as a 2,6-diphenoxyphenyl group and the like.

Examples of the aryl group having a nitrogen-containing group include a 4-(dimethylamino)phenyl group, a 4-nitrophenyl group and the like.

Examples of the aryl group having a silicon-containing group include a 3,5-bis(trimethylsilyl)phenyl group, a 3,5-bis(trimethylsiloxy)phenyl group and the like.

As the aromatic heterocyclic group in $R^2$, $R^3$ and $R^4$, preferred is an aromatic heterocyclic group having 3 to 20 carbon atoms, and concrete examples thereof include an imidazolyl group, a furyl group, a thienyl group, a pyridyl group and the like.

The aforementioned aromatic heterocyclic group may have an alkyl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the aromatic heterocyclic group having an alkyl group include an N-methylimidazolyl group and the like.

As the acyl group in $R^2$, $R^3$ and $R^4$, preferred are an alkylcarbonyl group having 2 to 20 carbon atoms and an arylcarbonyl group, and concrete examples thereof include an alkylcarbonyl group such as an acetyl group, a propionyl group, a butyryl group, an isobutyryl group, a pivaloyl group and the like; and an arylcarbonyl group such as a benzoyl group, a naphthoyl group, an anthrylcarbonyl group and the like.

The aforementioned alkylcarbonyl group may have, as a substituent on the alkyl group, a halogen atom such as a fluorine atom, a chlorine atom, a bromine atom, an iodine atom and the like.

Examples of the alkylcarbonyl group having a halogen atom include a trifluoroacetyl group and the like.

The aforementioned arylcarbonyl group may have, as a substituent on the aryl group, a halogen atom, an alkyl group having not more than 20 carbon atoms, an oxygen-containing group having not more than 20 carbon atoms, a nitrogen-containing group having not more than 20 carbon atoms, a silicon-containing group having not more than 20 carbon atoms and the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the arylcarbonyl group having a halogen atom include a pentafluorobenzoyl group and the like.

Examples of the arylcarbonyl group having an alkyl group include a 3,5-dimethylbenzoyl group, a 2,4,6-trimethylbenzoyl group and the like.

Examples of the arylcarbonyl group having an oxygen-containing group include a 2,6-dimethoxybenzoyl group, a 2,6-diisopropoxybenzoyl group and the like.

Examples of the arylcarbonyl group having a nitrogen-containing group include a 4-(dimethylamino)benzoyl group, a 4-cyanobenzoyl group and the like.

Examples of the arylcarbonyl group having a silicon-containing group include a 2,6-bis(trimethylsilyl)benzoyl group, a 2,6-bis(trimethylsiloxy)benzoyl group and the like.

As the alkoxycarbonyl group in $R^2$, $R^3$ and $R^4$, preferred is a linear, branched or cyclic alkoxycarbonyl group having 2 to 20 carbon atoms, and concrete examples thereof include a methoxycarbonyl group, an ethoxycarbonyl group, an n-butoxycarbonyl group, an n-octyloxycarbonyl group, an isopropoxycarbonyl group, a tert-butoxycarbonyl group, a cyclopentyloxycarbonyl group, a cyclohexyloxycarbonyl group, a cyclooctyloxycarbonyl group, an L-menthyloxycarbonyl group, a D-menthyloxycarbonyl group and the like.

The aforementioned alkoxycarbonyl group may have, as a substituent on the alkyl group, a halogen atom, an aryl group having not more than 20 carbon atoms, an aromatic heterocyclic group having not more than 20 carbon atoms, a non-aromatic heterocyclic group having not more than 20 carbon atoms and the like.

Examples of the halogen atom include a fluorine atom, a chlorine atom, a bromine atom, an iodine atom and the like. Examples of the alkoxycarbonyl group having a halogen atom include a 2,2,2-trifluoroethoxycarbonyl group and the like.

Examples of the alkoxycarbonyl group having an aryl group include unsubstituted or substituted aralkyloxycarbonyl groups such as a benzyloxycarbonyl group, a 4-methoxybenzyloxycarbonyl group, a 2-phenylethoxycarbonyl group, a cumyloxycarbonyl group, an α-naphthylmethoxycarbonyl group and the like.

Examples of the alkoxycarbonyl group having an aromatic heterocyclic group include a 2-pyridylmethoxycarbonyl group, a furfuryloxycarbonyl group, a 2-thienylmethoxycarbonyl group and the like.

Examples of the alkoxycarbonyl group having a non-aromatic heterocyclic group include a tetrahydrofurfuryloxycarbonyl group.

As an aryloxycarbonyl group in $R^2$, $R^3$ and $R^4$, preferred is an aryloxycarbonyl group having 7 to 20 carbon atoms, and concrete examples thereof include a phenoxycarbonyl group, an α-naphthyloxycarbonyl group and the like.

The aforementioned aryloxycarbonyl group may have, as a substituent on the aryl group, a halogen atom, an alkyl group having not more than 20 carbon atoms, an oxygen-containing group having not more than 20 carbon atoms, a nitrogen-containing group having not more than 20 carbon atoms, a silicon-containing group having not more than 20 carbon atoms and the like.

Examples of the halogen atom include a fluorine atom, a chlorine atom, a bromine atom, an iodine atom and the like.

Examples of the an oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the aryloxycarbonyl group having a halogen atom include a pentafluorophenoxycarbonyl group and the like.

Examples of the aryloxycarbonyl group having an alkyl group include a 2,6-dimethylphenoxycarbonyl group, a 2,4,6-trimethylphenoxycarbonyl group and the like.

Examples of the aryloxycarbonyl group having an oxygen-containing group include a 2,6-dimethoxyphenoxycarbonyl group, a 2,6-diisopropoxyphenoxycarbonyl group and the like.

Examples of the aryloxycarbonyl group having a nitrogen-containing group include a 4-(dimethylamino)phenoxycarbonyl group, a 4-cyanophenoxycarbonyl group and the like.

Examples of the aryloxycarbonyl group having a silicon-containing group include a 2,6-bis(trimethylsilyl)phenoxycarbonyl group, a 2,6-bis(trimethylsiloxy)phenoxycarbonyl group and the like.

Furthermore, two or more of $R^2$, $R^3$ and $R^4$ may be linked together to form a ring. The ring is preferably an aliphatic or aromatic hydrocarbon ring. The formed rings may be condensed to form a ring, respectively.

The aliphatic hydrocarbon ring is preferably a 10 or less-membered ring, particularly preferably a 3- to 7-membered ring, and most preferably a 5- or 6-membered ring. The aliphatic hydrocarbon ring may have unsaturated bonds.

The aromatic hydrocarbon ring is preferably a 6-membered ring, that is, a benzene ring.

For example, when $R^3$ and $R^4$ are linked together to form —$(CH_2)_4$— or —CH=CH—CH=CH—, a cyclohexene ring (included in the aliphatic hydrocarbon ring) or a benzene ring (included in the aromatic hydrocarbon ring) is formed, respectively.

The ring formed as described above may have one substituent or two or more substituents selected from a halogen atom, an alkyl group, an aryl group, an alkoxy group, an aryloxy group, an amino group, a nitro group, a cyano group, a silyl group and a silyloxy group.

Examples of the halogen atom include a fluorine atom, a chlorine atom, a bromine atom, an iodine atom and the like.

As the alkyl group, preferred is a linear, branched or cyclic alkyl group having not more than 20 carbon atoms which may have a substituent. Concrete examples thereof include a methyl group, an ethyl group, an n-propyl group, an isopropyl group, an n-butyl group, a sec-butyl group, a tert-butyl group, an n-pentyl group, a cyclopentyl group, a cyclohexyl group, an adamantyl group, a trifluoromethyl group, a benzyl group, a trityl group and the like.

As the aryl group, preferred is a substituted or unsubstituted aryl group having not more than 20 carbon atoms, and examples thereof include a phenyl group, a naphthyl group, a biphenyl group, an anthryl group, a 2,6-dimethylphenyl group, a 2,4,6-trimethylphenyl group, a 2,6-dimethoxyphenyl group and the like.

As the alkoxy group, preferred is a substituted or unsubstituted alkoxy group having not more than 20 carbon atoms, and examples thereof include a methoxy group, an ethoxy group, an isopropoxy group, a tert-butoxy group, a benzyloxy group and the like.

As the aryloxy group, preferred is a substituted or unsubstituted aryloxy group having not more than 20 carbon atoms, and examples thereof include a phenoxy group, a 2,6-dimethylphenoxy group and the like.

As the amino group, preferred is a substituted or unsubstituted amino group having not more than 20 carbon atoms, and examples thereof include a dimethylamino group, a diethylamino group, a diphenylamino group and the like.

As the silyl group, preferred is a silyl group having an alkyl group having not more than 20 carbon atoms or having an aryl group, and examples thereof include a trimethylsilyl group, a triethylsilyl group and the like.

As the silyloxy group, preferred is a silyloxy group having not more than 20 carbon atoms, and examples thereof include a trimethylsiloxy group and the like.

Furthermore, the aforementioned benzene ring may be condensed to form a condensed polycyclic ring such as a naphthalene ring.

[Hydrocarbon-Containing Group A*]

In the above general formula (b), A* represents an optically active hydrocarbon-containing group with three or more carbon atoms, and preferably 3 to 40 carbon atoms, having an asymmetric carbon atom or axial asymmetry which may have a substituent.

As the hydrocarbon-containing group in the above A*, optically active hydrocarbon-containing groups represented by the following general formulae (A-1) to (A-3) are suitable. In the formula, parts indicated as (N) and (OH) do not belong to A*, and represent a nitrogen atom and a hydroxyl group corresponding to those in the above general formula (b) to which A* is bonded,

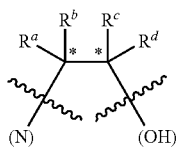
(A-1)

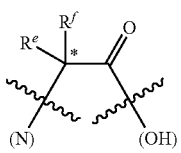
(A-2)

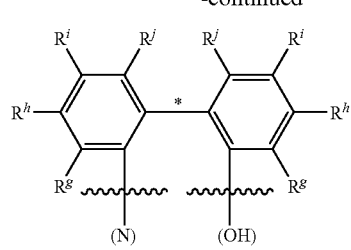
(A-3)

[Hydrocarbon-Containing Group A*: General Formula (A-1)]

In the above general formula (A-1), $R^a$, $R^b$, $R^c$ and $R^d$ are each a hydrogen atom, an alkyl group, an aryl group, an alkoxycarbonyl group, an aryloxycarbonyl group or an aminocarbonyl group, each of which may have a substituent.

Two or more of $R^a$, $R^b$, $R^c$ and $R^d$ may be linked together to form a ring and the ring may have a substituent.

Further, at least one of $R^a$, $R^b$, $R^c$ and $R^d$ is a different group, and both or at least one of the carbon atoms indicated as * become an asymmetric center.

An alkyl group, an aryl group, an alkoxycarbonyl group and an aryloxycarbonyl group in $R^a$, $R^b$, $R^c$ and $R^d$ are the same as the alkyl group, the aryl group, the alkoxycarbonyl group and the aryloxycarbonyl group as in the above $R^2$ to $R^4$.

As the aminocarbonyl group in $R^a$, $R^b$, $R^c$ and $R^d$, preferred is an aminocarbonyl group having a hydrogen atom, an alkyl group having not more than 20 carbon atoms or an aryl group having not more than 20 carbon atoms, and two of the substituents other than a carbonyl group to be bonded to a nitrogen atom may be linked together to form a ring. Concrete examples of the aminocarbonyl group having an alkyl group or an aryl group include an isopropylaminocarbonyl group, a cyclohexylaminocarbonyl group, a tert-butylaminocarbonyl group, a tert-amylaminocarbonyl group, a dimethylaminocarbonyl group, a diethylaminocarbonyl group, a diisopropylaminocarbonyl group, a diisobutylaminocarbonyl group, a dicyclohexylaminocarbonyl group, a tert-butylisopropylaminocarbonyl group, a phenylaminocarbonyl group, a pyrrolidylcarbonyl group, a piperidylcarbonyl group, an indolecarbonyl group and the like.

The aforementioned aminocarbonyl group may have, as a substituent on the aforementioned alkyl group or aryl group, a halogen atom, an aryl group having not more than 20 carbon atoms, an alkyl group having not more than 20 carbon atoms or the like.

Examples of the halogen atom include a fluorine atom, a chlorine atom, a bromine atom, an iodine atom and the like.

Examples of the aminocarbonyl group having an alkyl group which is substituted with a halogen atom include a 2-chloroethylaminocarbonyl group, a perfluoroethylaminocarbonyl group and the like.

Examples of the aminocarbonyl group having an aryl group which is substituted with a halogen atom include a 4-chlorophenylaminocarbonyl group, a pentafluorophenylaminocarbonyl group and the like.

Examples of the aminocarbonyl group having an alkyl group which is substituted with an aryl group include substituted or unsubstituted aralkylaminocarbonyl groups such as a benzylaminocarbonyl group, a 2-phenylethylaminocarbonyl group, an α-naphthylmethylaminocarbonyl group and the like.

Examples of the aminocarbonyl group having an aryl group which is substituted with an alkyl group include a 2,4,6-trimethylphenylaminocarbonyl group and the like.

Meanwhile, two or more of $R^a$, $R^b$, $R^c$ and $R^d$ may be linked together to form a ring. The ring is preferably aliphatic hydrocarbon and the formed ring may be further condensed to form a ring. The ring is preferably a 3- to 7-membered ring and particularly preferably a 5- or 6-membered ring. For example, when $R^a$ and $R^c$ are linked together to form —(CH$_2$)$_3$—, a 5-membered ring is formed.

The thus formed ring may have one substituent or two or more substituents selected from a halogen atom, an alkyl group, an aryl group, an alkoxy group, an aryloxy group, an amino group, a nitro group, a cyano group, a silyl group and a silyloxy group.

Concrete examples of the optically active hydrocarbon-containing group represented by the above general formula (A-1) include those represented by the following formulas (A-1a) to (A-1x), their enantiomers and the like.

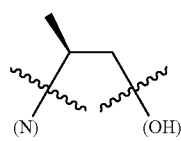
(A-1a)

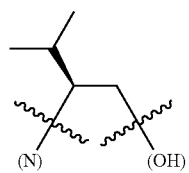
(A-1b)

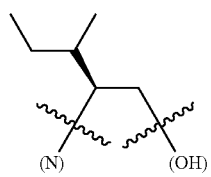
(A-1c)

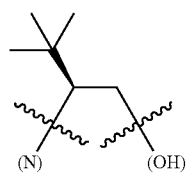
(A-1d)

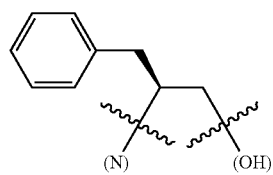
(A-1e)

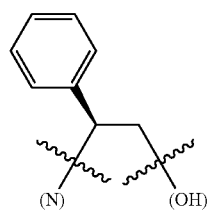
(A-1f)

-continued

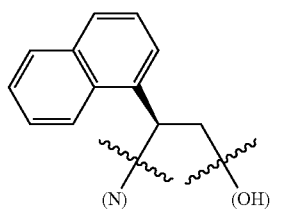
(A-1g)

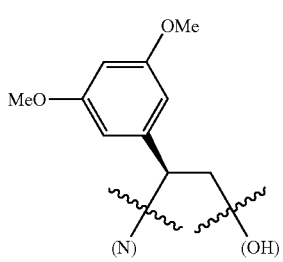
(A-1h)

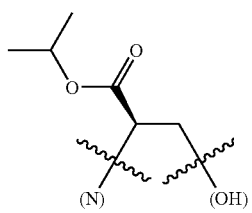
(A-1i)

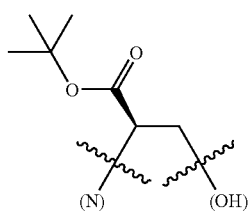
(A-1j)

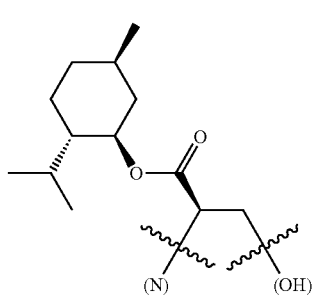
(A-1k)

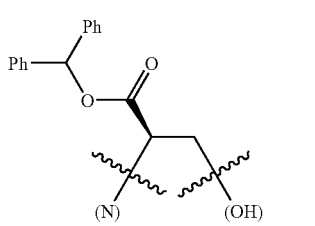
(A-1l)

-continued (A-1m)
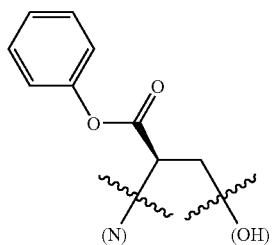

(A-1n)
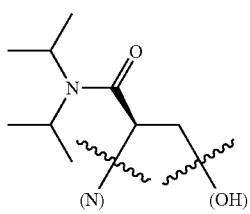

(A-1o)
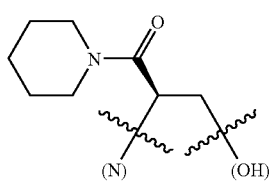

(A-1p)
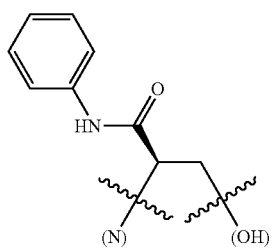

(A-1q)
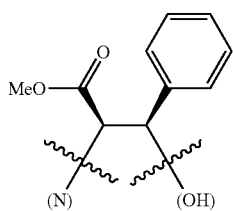

(A-1r)
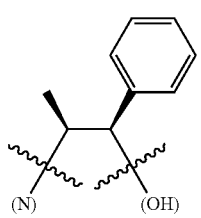

(A-1s)
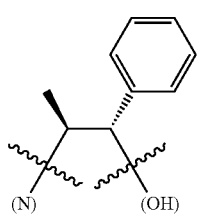

-continued (A-1t)
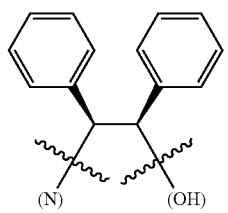

(A-1u)
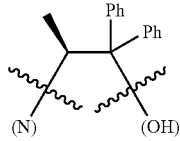

(A-1v)
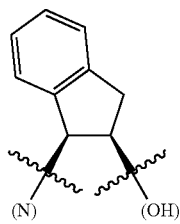

(A-1w)
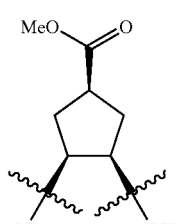

(A-1x)
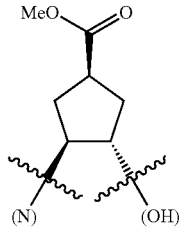

[Hydrocarbon-Containing Group A*: General Formula (A-2)]

In the above general formula (A-2), $R^e$ and $R^f$ are each a hydrogen atom, an alkyl group or an aryl group, each of which may have a substituent. Furthermore, $R^e$ and $R^f$ are different substituents, and * represents an asymmetric carbon atom.

The alkyl group and aryl group in $R^e$ and $R^f$ are the same as the alkyl group and aryl group in the above $R^a$ to $R^d$.

Concrete examples of the optically active hydrocarbon-containing group represented by the above general formula (A-2) include those represented by the following formulas (A-2a) to (A-2p), their enantiomers and the like.

(A-2a)
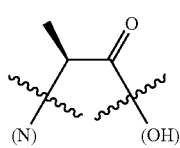

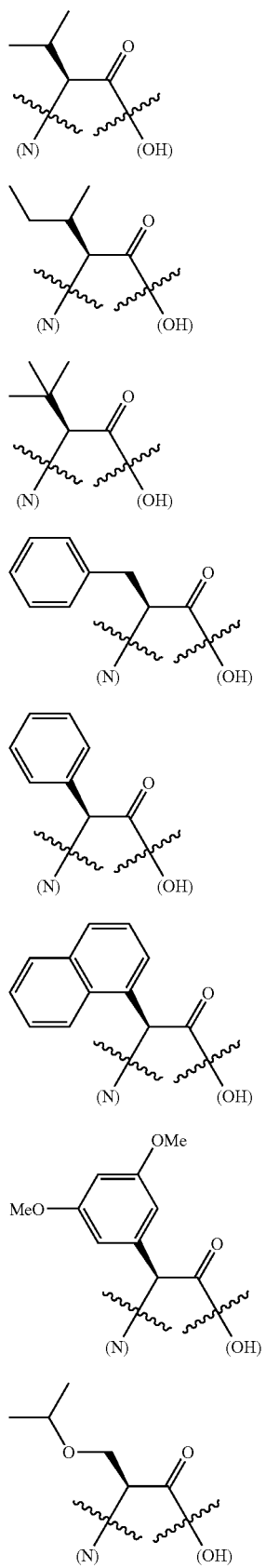
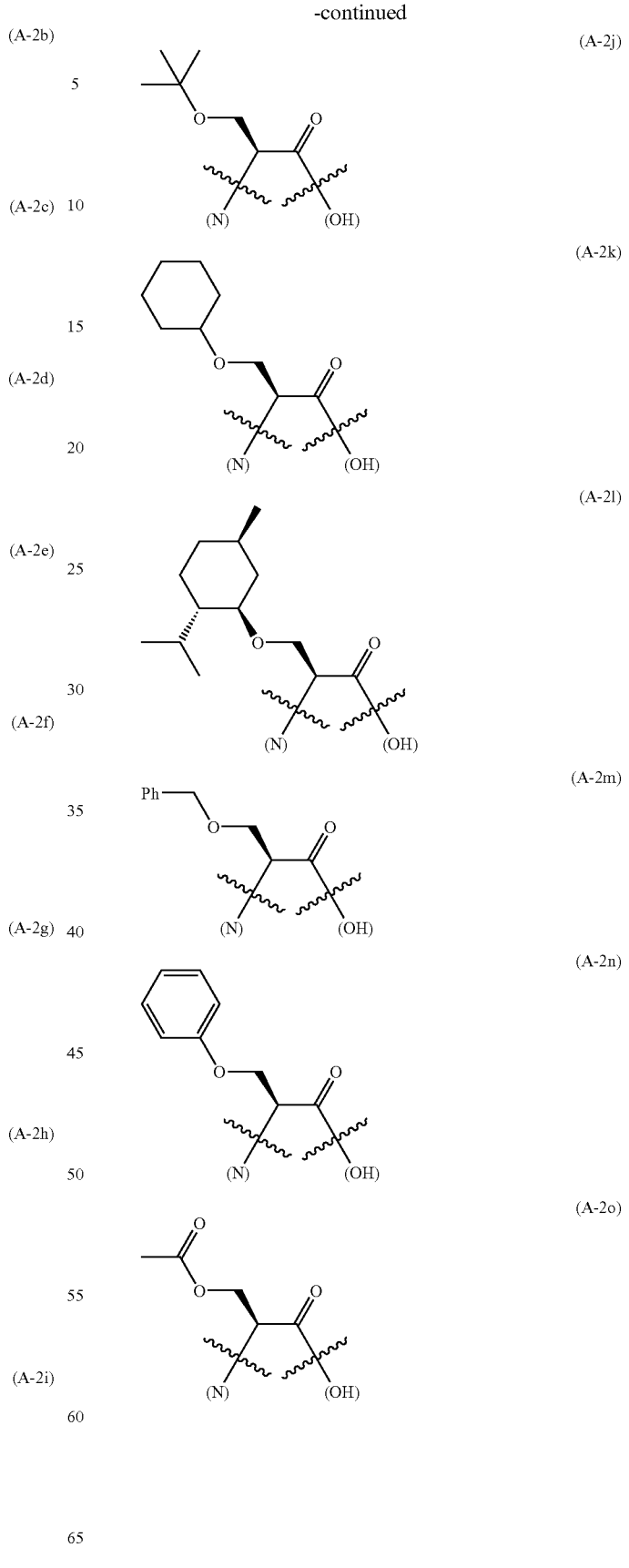

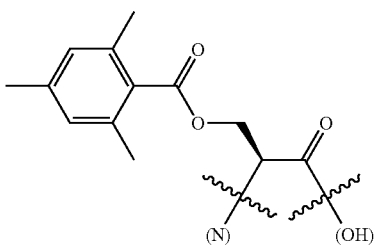

(A-2p)

[Hydrocarbon-Containing Group A*: General Formula (A-3)]

In the above general formula (A-3), $R^g$, $R^h$, $R^i$ and $R^j$ are independently a hydrogen atom, a halogen atom, an alkyl group, an aryl group or an alkoxy group, each of which may have a substituent. Further, $R^i$ and $R^j$ on the same benzene ring may be linked together or condensed to form a ring. *' represents an axial asymmetry.

Examples of the halogen atom in $R^g$, $R^h$, $R^i$ and $R^j$ include a fluorine atom, a chlorine atom, a bromine atom, an iodine atom and the like.

The alkyl group and aryl group in $R^g$, $R^h$, $R^i$ and $R^j$ are the same as the alkyl group and the aryl group in the above $R^2$ to $R^4$.

As the alkoxy group in $R^g$, $R^h$, $R^i$ and $R^j$, preferred is an alkoxy group having not more than 20 carbon atoms, and examples thereof include a methoxy group, an ethoxy group, and n-propoxy group, an isopropoxy group, a tert-butoxy group and the like.

Furthermore, when $R^i$ and $R^j$ on the same benzene ring are linked together to form a ring, the ring is preferably an aliphatic or aromatic hydrocarbon ring, or a non-aromatic heterocyclic containing an oxygen atom. The formed rings may be condensed to form a ring.

The aliphatic hydrocarbon ring is preferably a 5- or 6-membered ring.

The aromatic hydrocarbon ring is preferably a 6-membered ring, that is, a benzene ring.

For example, when $R^i$ and $R^j$ are linked together to form —CH=CH—CH=CH—, —(CH$_2$)$_4$— or —OCH$_2$O—, a naphthalene ring, a tetrahydronaphthalene ring or a benzodioxorane ring is formed, respectively.

The thus formed ring such as a naphthalene ring, a tetrahydronaphthalene ring, a benzodioxorane ring or the like may have one substituent or two or more substituents selected from, for example, a halogen atom, an alkyl group, an aryl group and an alkoxy group.

Examples of the halogen atom include a fluorine atom, a chlorine atom, a bromine atom, an iodine atom and the like.

As the alkyl group, preferred is a linear, branched or cyclic alkyl group having not more than 20 carbon atoms which may have a substituent. Concrete examples thereof include a methyl group, an ethyl group, an n-propyl group, an isopropyl group, a tert-butyl group, a cyclopentyl group, a cyclohexyl group and the like.

As the aryl group, preferred is a substituted or unsubstituted aryl group having not more than 20 carbon atoms, and concrete examples thereof include a phenyl group, a naphthyl group, a biphenyl group, an anthryl group and the like.

As the alkoxy group, preferred is a substituted or unsubstituted alkoxy group having not more than 20 carbon atoms, and concrete examples thereof include a methoxy group, an ethoxy group, an n-propoxy group, an isopropoxy group, a tert-butoxy group and the like.

Meanwhile, the benzene rings may be condensed to form a condensed polycyclic ring such as a naphthalene ring and the like.

Concrete examples of the optically active hydrocarbon-containing group represented by the above general formula (A-3) include those represented by the following formulas (A-3a) to (A-3c), their enantiomers and the like.

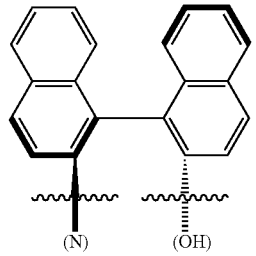

(A-3a)

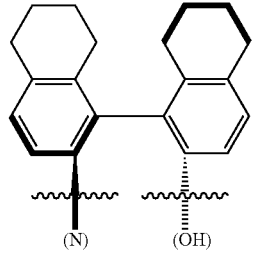

(A-3b)

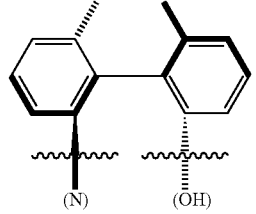

(A-3c)

[Optically Active Ligand Represented by the General Formula (c)]

Preferred examples of the optically active ligand represented by the general formula (b) include optically active ligands represented by the above general formula (c).

$R^a$, $R^b$, $R^c$ and $R^d$ in the above general formula (c) represent the same as those in the above general formula (A-1). Namely, $R^a$, $R^b$, $R^c$ and $R^d$ are each a hydrogen atom, an alkyl group, an aryl group, an alkoxycarbonyl group, an aryloxycarbonyl group or an aminocarbonyl group, each of which may have a substituent. Two or more of $R^a$, $R^b$, $R^c$ and $R^d$ may be linked together to form a ring and the ring may have a substituent. Furthermore, at least one of $R^a$, $R^b$, $R^c$ and $R^d$ is a different group. Both or at least one of the carbon atoms indicated as * become an asymmetric center.

$R^5$ in the above general formula (c) is a hydrogen atom or an alkyl and the alkyl group may have a substituent.

$R^6$, $R^7$, $R^8$ and $R^9$ in the above general formula (c) are independently a hydrogen atom, a halogen atom, an alkyl group, an alkenyl group, an aryl group, an aromatic heterocyclic group, a non-aromatic heterocyclic group, an alkoxycarbonyl group, an aryloxycarbonyl group, a hydroxyl group, an alkoxy group, an aryloxy group, an amino group, a cyano group, a nitro group, a silyl group or a siloxy group which may have a substituent, each of which may be linked together to form a ring.

As the alkyl group in $R^5$, preferred is a linear, branched or cyclic alkyl group having not more than 20 carbon atoms, and concrete examples thereof include a methyl group, an ethyl group, an n-propyl group, an isopropyl group, a sec-butyl group, a cyclopropyl group, a cyclopentyl group, a cyclohexyl group and the like.

The aforementioned linear, branched or cyclic alkyl group may have, as a substituent, a halogen atom, an aryl group having not more than 20 carbon atoms, an aromatic heterocyclic group having not more than 20 carbon atoms, a non-aromatic heterocyclic group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the alkyl group having a halogen atom include a chloromethyl group, a 2-chloroethyl group, a trifluoromethyl group, a 2,2,2-trifluoroethyl group, a perfluoroethyl group, a perfluorohexyl group and the like.

Examples of the alkyl group having an aryl group include substituted or unsubstituted aralkyl groups such as a benzyl group, a 4-methoxybenzyl group, a 2-phenylethyl group, a cumyl group, an α-naphthylmethyl group, a trityl group and the like.

Examples of the alkyl group having an aromatic heterocyclic group include a 2-pyridylmethyl group, a furfuryl group, a 2-thienylmethyl group and the like.

Examples of the alkyl group having a non-aromatic heterocyclic group include a tetrahydrofurfuryl group and the like.

Examples of the alkyl group having an oxygen-containing group include a methoxyethyl group, a phenoxyethyl group and the like.

Examples of the alkyl group having a nitrogen-containing group include a 2-(dimethylamino)ethyl group, a 3-(diphenylamino)propyl group and the like.

Examples of the alkyl group having a silicon-containing group include a 2-(trimethylsiloxy)ethyl group and the like.

Examples of the halogen atom in $R^6$, $R^7$, $R^8$ and $R^9$ include a fluorine atom, a chlorine atom, a bromine atom, an iodine atom and the like.

As the alkyl group in $R^6$, $R^7$, $R^8$ and $R^9$, preferred is a linear, branched or cyclic alkyl group having not more than 20 carbon atoms, and concrete examples thereof include a methyl group, an ethyl group, an n-propyl group, an isopropyl group, a sec-butyl group, a tert-butyl group, a cyclopentyl group, a cyclohexyl group, an adamantyl group and the like.

The aforementioned linear, branched or cyclic alkyl group may have, as a substituent, a halogen atom, an aryl group having not more than 20 carbon atoms, an aromatic heterocyclic group having not more than 20 carbon atoms, a non-aromatic heterocyclic group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the alkyl group having a halogen atom include halogenated alkyl groups having not more than 20 carbon atoms such as a chloromethyl group, a 2-chloroethyl group, a trifluoromethyl group, a 2,2,2-trifluoroethyl group, a perfluoroethyl group, a perfluorohexyl group and the like.

Examples of the alkyl group having an aryl group include substituted or unsubstituted aralkyl groups such as a benzyl group, a 4-methoxybenzyl group, a 2-phenylethyl group, a cumyl group, an α-naphthylmethyl group, a 2-phenylisopropyl group, a trityl group, a 2-phenylnaphthalene-1-yl group and the like.

Examples of the alkyl group having an aromatic heterocyclic group include a 2-pyridylmethyl group, a furfuryl group, a 2-thienylmethyl group and the like. Examples of the alkyl group having a non-aromatic heterocyclic group include a tetrahydrofurfuryl group and the like. Examples of the alkyl group having an oxygen-containing group include a methoxyethyl group, a phenoxyethyl group and the like. Examples of the alkyl group having a nitrogen-containing group include a 2-(dimethylamino)ethyl group, a 3-(diphenylamino)propyl group and the like. Examples of the alkyl group having a silicon-containing group include a 2-(trimethylsiloxy)ethyl group and the like.

As the alkenyl group in $R^6$, $R^7$, $R^8$ and $R^9$, preferred is a linear or branched alkenyl group having 2 to 20 carbon atoms, and concrete examples thereof include a vinyl group, an allyl group, an isopropenyl group and the like.

The aforementioned linear or branched alkenyl group may have, as a substituent, a halogen atom, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the alkenyl group having a halogen atom include a 2-chlorovinyl group, a 2,2-dichlorovinyl group, a 3-chloroisopropenyl group and the like.

As the aryl group in $R^6$, $R^7$, $R^8$ and $R^9$, preferred is an aryl group having 6 to 20 carbon atoms, and concrete examples thereof include a phenyl group, a naphthyl group, a biphenyl group, an anthryl group, a 2-phenyl-1-naphthyl group and the like.

The aforementioned aryl group may have, as a substituent, a halogen atom, an alkyl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the aryl group having a halogen atom include a pentafluorophenyl group and the like. Examples of the aryl group having an alkyl group include a tolyl group, a dimethylphenyl group, a 2,4,6-trimethylphenyl group, an isopropylphenyl group, a diisopropylphenyl group, a tert-butylphenyl group, a di-tert-butylphenyl group and the like.

Examples of the aryl group having an oxygen-containing group include an alkoxy-substituted aryl group such as a 4-methoxyphenyl group, a 3,5-dimethoxyphenyl group, a 3,5-diisopropoxyphenyl group, a 2,4,6-triisopropoxyphenyl group and the like; and an aryloxy-substituted aryl group such as a 2,6-diphenoxyphenyl group and the like.

Examples of the aryl group having a nitrogen-containing group include a 4-(dimethylamino)phenyl group, a 4-nitrophenyl group and the like.

Examples of the aryl group having a silicon-containing group include a 3,5-bis(trimethylsilyl)phenyl group, a 3,5-bis(trimethylsiloxy)phenyl group and the like.

As the aromatic heterocyclic group in $R^6$, $R^7$, $R^8$ and $R^9$, preferred is an aromatic heterocyclic group having 3 to 20 carbon atoms, and concrete examples thereof include an imidazolyl group, a furyl group, a thienyl group, a pyridyl group and the like.

The aforementioned aromatic heterocyclic group may have an alkyl group having not more than 20 carbon atoms, an aryl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the aromatic heterocyclic group having an alkyl group include an N-methylimidazolyl group and the like.

As the non-aromatic heterocyclic group in $R^6$, $R^7$, $R^8$ and $R^9$, preferred is a non-aromatic heterocyclic group having 4 to 20 carbon atoms, and concrete examples thereof include a pyrrolidinyl group, a piperidyl group, a tetrahydrofuryl group, a tetrahydropyranyl group and the like.

The aforementioned non-aromatic heterocyclic group may have an alkyl group having not more than 20 carbon atoms, an aryl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the non-aromatic heterocyclic group having an aryl group include aryl-substituted non-aromatic heterocyclic groups having not more than 20 carbon atoms such as an N-phenyl-4-piperidyl group and the like.

As the alkoxycarbonyl group in $R^6$, $R^7$, $R^8$ and $R^9$, preferred is a linear, branched or cyclic alkoxycarbonyl group having 2 to 20 carbon atoms, and concrete examples thereof include a methoxycarbonyl group, an ethoxycarbonyl group, an n-butoxycarbonyl group, an n-octyloxycarbonyl group, an isopropoxycarbonyl group, a tert-butoxycarbonyl group, a cyclopentyloxycarbonyl group, a cyclohexyloxycarbonyl group, a cyclooctyloxycarbonyl group and the like.

The aforementioned alkoxycarbonyl group may have, as a substituent on the alkyl group, a halogen atom, an aryl group having not more than 20 carbon atoms, an aromatic heterocyclic group having not more than 20 carbon atoms, a non-aromatic heterocyclic group having not more than 20 carbon atoms or the like.

Examples of the halogen atom include a fluorine atom, a chlorine atom, a bromine atom, an iodine atom and the like.

Examples of the alkoxycarbonyl group having a halogen atom include a 2,2,2-trifluoroethoxycarbonyl group and the like.

Examples of the alkoxycarbonyl group having an aryl group include substituted or unsubstituted aralkyloxycarbonyl groups such as a benzyloxycarbonyl group, a 4-methoxybenzyloxycarbonyl group, a 2-phenylethoxycarbonyl group, a cumyloxycarbonyl group, an α-naphthylmethoxycarbonyl group and the like.

Examples of the alkoxycarbonyl group having an aromatic heterocyclic group include a 2-pyridylmethoxycarbonyl group, a furfuryloxycarbonyl group, a 2-thienylmethoxycarbonyl group and the like.

Examples of the alkoxycarbonyl group having a non-aromatic heterocyclic group include a tetrahydrofurfuryloxycarbonyl group and the like.

As the aryloxycarbonyl group in $R^6$, $R^7$, $R^8$ and $R^9$, preferred is an aryloxycarbonyl group having 7 to 20 carbon atoms, and concrete examples thereof include a phenoxycarbonyl group, an α-naphthyloxycarbonyl group and the like.

The aforementioned aryloxycarbonyl group may have, as a substituent on the aryl group, a halogen atom, an alkyl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the aryloxycarbonyl group having a halogen atom include a pentafluorophenoxycarbonyl group and the like.

Examples of the aryloxycarbonyl group having an alkyl group include a 2,6-dimethylphenoxycarbonyl group, a 2,4,6-trimethylphenoxycarbonyl group and the like.

Examples of the aryloxycarbonyl group having an oxygen-containing group include a 2,6-dimethoxyphenoxycarbonyl group, a 2,6-diisopropoxyphenoxycarbonyl group and the like. Examples of the aryloxycarbonyl group having a nitrogen-containing group include a 4-(dimethylamino)phenoxycarbonyl group, a 4-cyanophenoxycarbonyl group and the like. Examples of the aryloxycarbonyl group having a silicon-containing group include a 2,6-bis(trimethylsilyl)phenoxycarbonyl group, a 2,6-bis(trimethylsiloxy)phenoxycarbonyl group and the like.

As the alkoxy group in $R^6$, $R^7$, $R^8$ and $R^9$, preferred is a linear, branched or cyclic alkoxy group having not more than 20 carbon atoms. Concrete examples thereof include a methoxy group, an ethoxy group, an n-propoxy group, an isopropoxy group, a tert-butoxy group, a cyclopentyloxy group, a cyclohexyloxy group, a methyloxy group and the like.

The aforementioned alkoxy group may have, as a substituent on the alkyl group, a halogen atom, an aryl group having not more than 20 carbon atoms, an aromatic heterocyclic group having not more than 20 carbon atoms, a non-aromatic heterocyclic group having not more than 20 carbon atoms or the like.

Examples of the halogen atom include a fluorine atom, a chlorine atom, a bromine atom, an iodine atom and the like.

Examples of the alkoxy group having a halogen atom include a 2,2,2-trifluoroethoxy group and the like.

Examples of the alkoxy group having an aryl group include substituted or unsubstituted aralkyloxy groups such as a benzyloxy group, a 4-methoxybenzyloxy group, a 2-phenylethoxy group, a cumyloxy group, an α-naphthylmethoxy and the like.

Examples of the alkoxy group having an aromatic heterocyclic group include a 2-pyridylmethoxy group, a furfuryloxy group, a 2-thienylmethoxy group and the like.

Examples of the alkoxy group having a non-aromatic heterocyclic group include a tetrahydrofurfuryloxy group and the like.

As the aryloxy group in $R^6$, $R^7$, $R^8$ and $R^9$, preferred is an aryloxy group having 6 to 20 carbon atoms. Concrete examples thereof include a phenoxy group, a naphthyloxy group and the like.

The aforementioned aryloxy group may have, as a substituent on the aryl group, a halogen atom, an alkyl group having not more than 20 carbon atoms, an oxygen-containing group having not more than 20 carbon atoms, a nitrogen-containing group having not more than 20 carbon atoms, a silicon-containing group having not more than 20-carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the aryloxy group having a halogen atom include halogenated aryloxy groups such as a pentafluorophenoxy group and the like.

Examples of the aryloxy group having an alkyl group include alkyl-substituted aryloxy groups such as a 2,6-dimethylphenoxy group, a 2,4,6-trimethylphenoxy group and the like.

Examples of the aryloxy group having an oxygen-containing group include a 2,6-dimethoxyphenoxy group, a 2,6-diisopropoxyphenoxy group and the like.

Examples of the aryloxy group having a nitrogen-containing group include a 4-(dimethylamino)phenoxy group, a 4-cyanophenoxy group and the like.

Examples of the aryloxy group having a silicon-containing group include a 2,6-bis(trimethylsilyl)phenoxy group, a 2,6-bis(trimethylsiloxy)phenoxy group and the like.

As the amino group in $R^6$, $R^7$, $R^8$ and $R^9$, preferred is a hydrogen atom, a linear, branched or cyclic alkyl group having not more than 20 carbon atoms, or an amino group having an aryl group. Two substituents to be bonded to a nitrogen atom may be linked together to form a ring. Concrete examples of the amino group having an alkyl group or an aryl group include an isopropylamino group, a cyclohexylamino group, a tert-butylamino group, a tert-amylamino group, a dimethylamino group, a diethylamino group, a diisopropylamino group, a diisobutylamino group, a dicyclohexylamino group, a tert-butylisopropylamino group, a pyrrolidyl group, a piperidyl group, an indole group and the like.

The aforementioned amino group may have, as a substituent on the aforementioned alkyl group or aryl group, a halogen atom, an aryl group having not more than 20 carbon atoms, an alkyl group having not more than 20 carbon atoms or the like.

Examples of the amino group having an alkyl group which is substituted with a halogen atom include a 2,2,2-trichloroethylamino group, a perfluoroethylamino group and the like.

Examples of the amino group having an aryl group which is substituted with a halogen atom include a pentafluorophenylamino group and the like. Examples of the amino group having an alkyl group which is substituted with an aryl group include substituted or unsubstituted aralkylamino groups such as a benzylamino group, a 2-phenylethylamino group, an α-naphthylmethylamino group and the like.

Examples of the amino group having an aryl group which is substituted with an alkyl group include a 2,4,6-trimethylphenylamino group and the like.

As the silyl group in $R^6$, $R^7$, $R^8$ and $R^9$, preferred is a silyl group having not more than 20 carbon atoms, and concrete examples thereof include a trimethylsilyl group, a tert-butyldimethylsilyl group and the like.

As the siloxy group in $R^6$, $R^7$, $R^8$ and $R^9$, preferred is a siloxy group having not more than 20 carbon atoms, and concrete examples thereof include a trimethylsiloxy group, a tert-butyldimethylsiloxy group, a tert-butyldiphenylsiloxy group and the like.

Furthermore, two or more of $R^6$, $R^7$, $R^8$ and $R^9$ may be linked together to form a ring. The ring is preferably an aliphatic or aromatic hydrocarbon ring. The formed rings may be condensed to form a ring The aliphatic hydrocarbon ring is preferably a 10 or less-membered ring, particularly preferably a 3- to 7-membered ring, and most preferably a 5- or 6-membered ring. The aliphatic hydrocarbon ring may have unsaturated bonds.

The aromatic hydrocarbon ring is preferably a 6-membered ring, that is, a benzene ring.

For example, when $R^7$ and $R^8$ are linked together to form —$(CH_2)_4$— or —CH=CH—CH=CH—, a cyclohexene ring (included in the aliphatic hydrocarbon ring) or a benzene ring (included in the aromatic hydrocarbon ring) is formed, respectively.

The thus formed ring may have one group or two or more groups selected from a halogen atom, an alkyl group, an aryl group, an alkoxy group, an aryloxy group, an amino group, a nitro group, a cyano group, a silyl group and a silyloxy group.

Examples of the halogen atom include a fluorine atom, a chlorine atom, a bromine atom, an iodine atom and the like.

As the alkyl group, preferred is a linear, branched or cyclic alkyl group having not more than 20 carbon atoms which may have a substituent. Concrete examples thereof include a methyl group, an ethyl group, an n-propyl group, an isopropyl group, an n-butyl group, a sec-butyl group, a tert-butyl group, an n-pentyl group, a cyclopentyl group, a cyclohexyl group, an adamantyl group, a trifluoromethyl group, a benzyl group, a trityl group and the like.

As the aryl group, preferred is a substituted or unsubstituted aryl group having not more than 20 carbon atoms, and examples thereof include a phenyl group, a naphthyl group, a biphenyl group, an anthryl group, a 2,6-dimethylphenyl group, a 2,4,6-trimethylphenyl group, a 2,6-dimethoxyphenyl group and the like.

As the alkoxy group, preferred is a substituted or unsubstituted alkoxy group having not more than 20 carbon atoms, and examples thereof include a methoxy group, an ethoxy group, an isopropoxy group, a tert-butoxy group, a benzyloxy group and the like. As the aryloxy group, preferred is a substituted or unsubstituted aryloxy group having not more than 20 carbon atoms, and examples thereof include a phenoxy group, a 2,6-dimethylphenoxy group and the like.

As the amino group, preferred is a substituted or unsubstituted amino group having not more than 20 carbon atoms, and examples thereof include a dimethylamino group, a diethylamino group, a diphenylamino group and the like.

As the silyl group, preferred is a silyl group having an alkyl group or aryl group having not more than 20 carbon atoms, and examples thereof include a trimethylsilyl group, a triethylsilyl group and the like.

As the silyloxy group, preferred is a silyloxy group having not more than 20 carbon atoms, and examples thereof include a trimethylsiloxy group and the like.

In addition, the aforementioned benzene rings may be condensed to form a condensed polycyclic ring such as a naphthalene ring and the like.

More preferable examples of the optically active ligand represented by the above general formula (c) include those with $R^9$ of a substituted or unsubstituted alkyl group and aryl group.

[Concrete Examples of the Optically Active Ligand Represented by the General Formulae (b) and (c)]

Concrete examples of the optically active ligand represented by the above general formulae (b) and (c) include those represented by the following formulae (b-1) to (b-3) and their enantiomers, those represented by the following formulae (c-1) to (c-20) and their enantiomers, and the like.

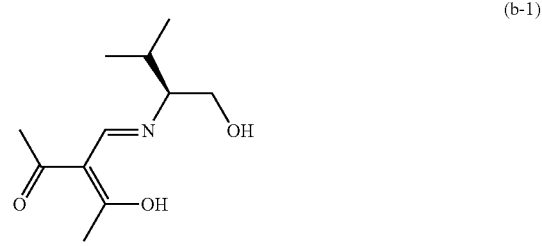

(b-1)

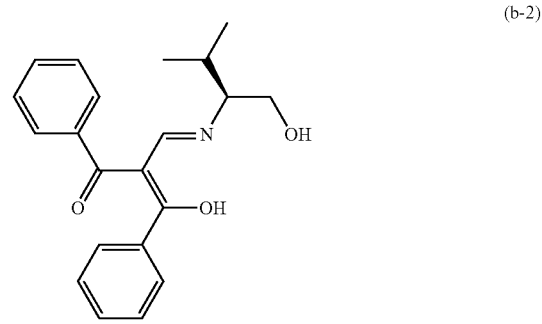

(b-2)

(b-3)
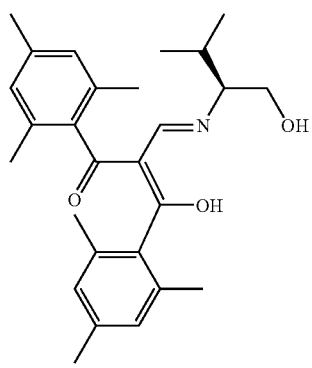
(c-1)
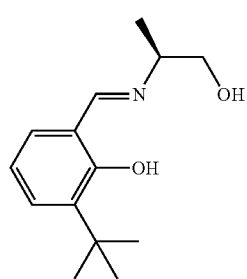
(c-2)
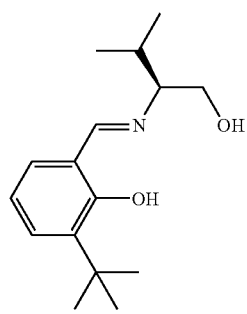
(c-3)
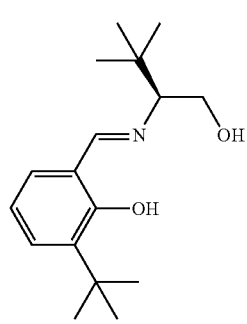
(c-4)
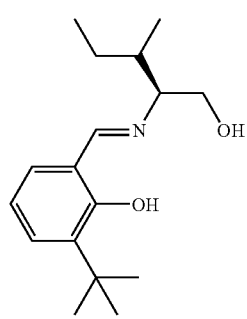
(c-5)
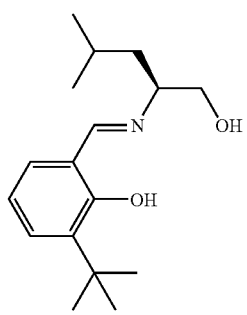
(c-6)
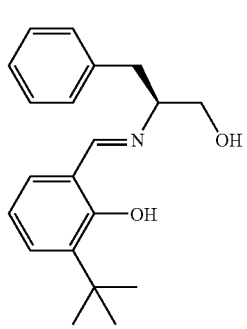
(c-7)
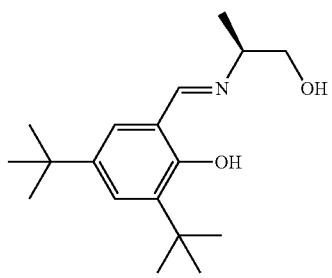
(c-8)
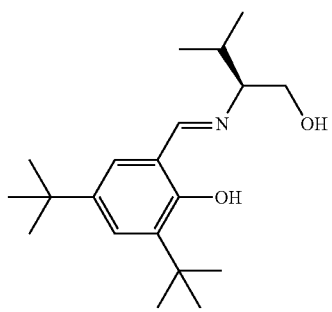
(c-9)
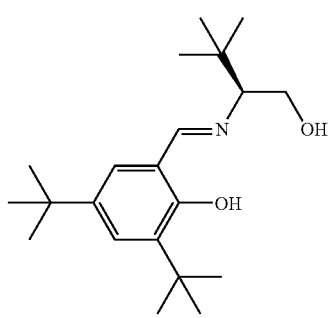

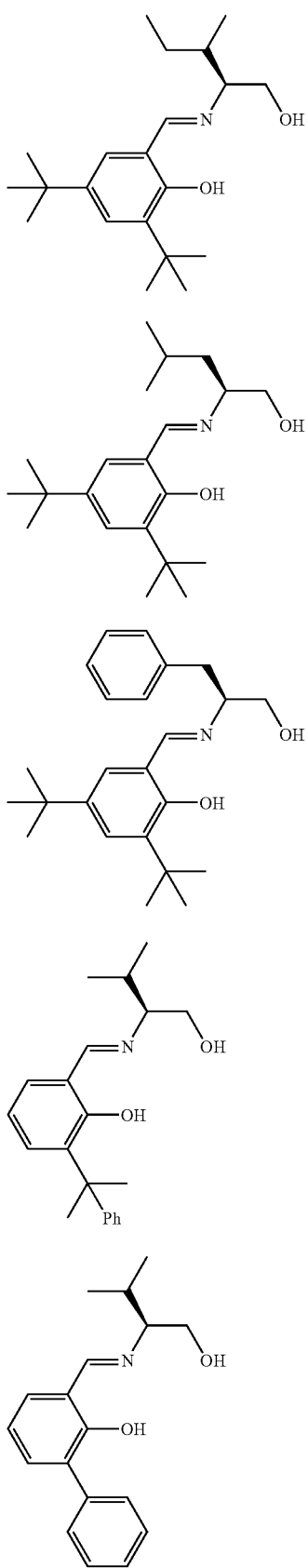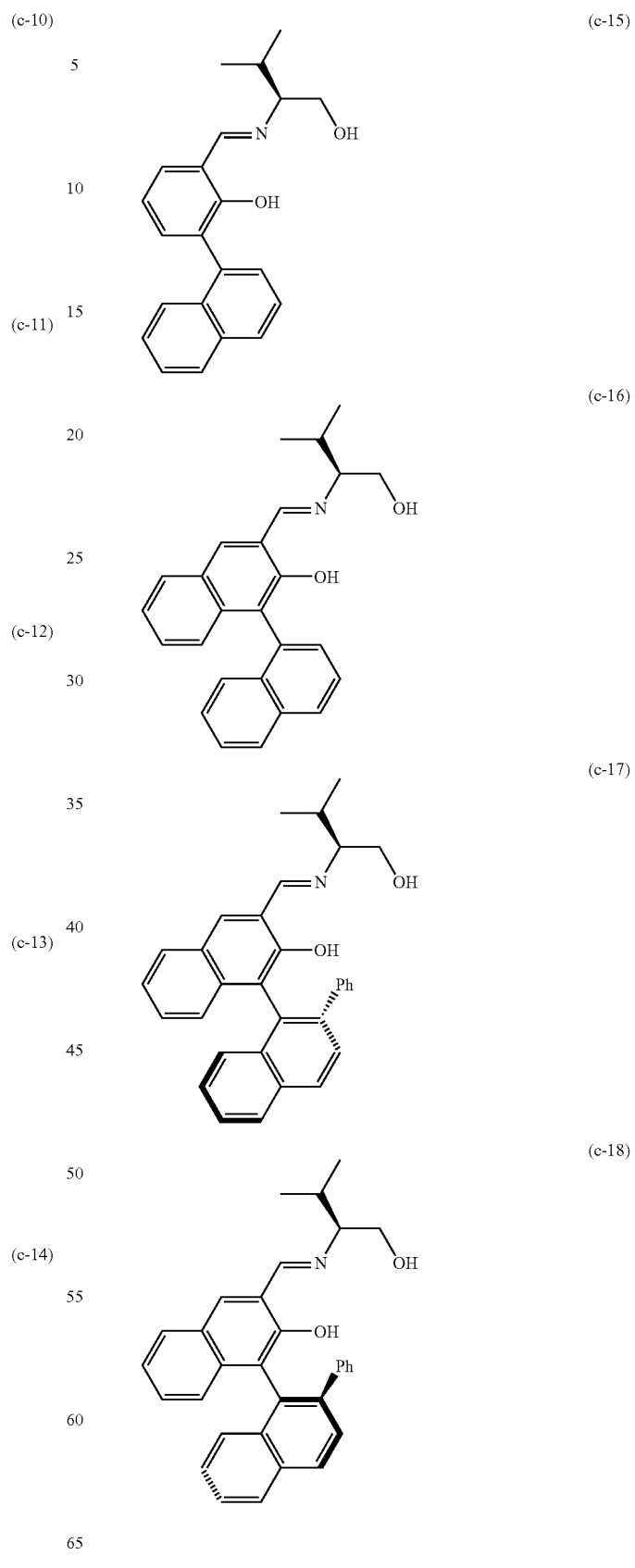

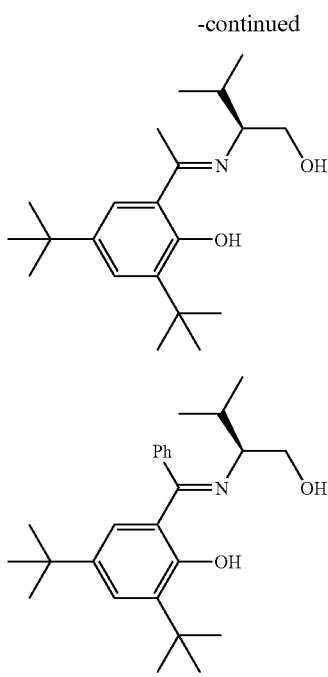

(c-19)

(c-20)

[Process for Producing a Titanium Compound]

The aforementioned titanium tetraalkoxide compound can be produced according to the known method. For example, it can be produced, in the presence or absence of a base, by adding the corresponding alcohol to titanium tetrachloride in a prescribed amount, stirring the resulting mixture, and then purifying it by distillation. According to the present invention, it is also possible to use a solution prepared from titanium tetrachloride and alcohol as it is without purification for the production of an optically active titanium compound.

The titanium oxoalkoxide compound represented by the above general formula (a) can be produced according to the known method. For example, there have been known a method comprising hydrolyzing titanium tetraalkoxide in alcohol (J. Am. Chem. Soc., Vol. 113, p. 8190 (1991)), a method comprising reacting titanium tetraalkoxide with a carboxylic acid (J. Chem. Soc. Dalton Trans., p. 3653 (1999)) and the like.

The obtained titanium oxoalkoxide compound may be used as it is without purification for the production of an optically active titanium compound or may be purified according to the known purification method such as recrystallization or the like, prior to use.

The optically active ligand represented by the above general formula (b) or (c) can be produced by the known method. For example, the optically active ligand represented by the above general formula (b) can be synthesized from an optically active amino alcohol and a 1,3-diketone derivative in one step by a dehydration reaction. Further, the optically active ligand represented by the general formula (c) can be synthesized from an optically active amino alcohol and an o-hydroxybenzaldehyde derivative, or from amino alcohol and an o-hydroxyphenyl ketone derivative in one step by a dehydration reaction (for example, disclosed in the above Patent Document 1).

The optically active amino alcohol is obtained, for example, by reducing a carboxylic group of a natural or non-natural α-amino acid and various kinds thereof are industrially available. As the 1,3-diketone derivative, 2-acetyl-3-oxo-butylaldehyde can be cited.

[Production from a Titanium Tetraalkoxide Compound]

The titanium compound of the present invention can be produced by reacting the above titanium tetraalkoxide compound and preferably the titanium tetraalkoxide compound represented by the general formula (a') with water in an organic solvent, and then mixing with the optically active ligand represented by the above general formula (b) or (c). The mole ratio of the titanium tetraalkoxide compound, water and the optically active ligand represented by the above general formula (b) or (c) is preferably in the range of 1: (0.1~2.0): (0.1~3.0).

Firstly, a titanium tetraalkoxide compound is reacted with water in an organic solvent. At that time, water is contained preferably in an amount of from 0.1 to 2.0 moles and more preferably from 0.2 to 1.5 moles, based on 1 mole of the titanium tetraalkoxide compound. Water in that amount is added and stirred. At that time, the titanium tetraalkoxide compound is preferably dissolved in a solvent in advance and water is preferably diluted in a solvent, prior to add. Water can also be directly added by a method comprising adding water in mist form, a method comprising using a reaction vessel equipped with a high efficiency stirrer or the like. Instead of adding water, an inorganic salt containing water of crystallization, undehydrated silica gel, zeolite of a moisture-absorbed molecular sieve or the like can also be used. Preferable examples of the organic solvent in use include halogenated hydrocarbon solvents such as dichloromethane, chloroform, fluorobenzene, trifluoromethylbenzene and the like; aromatic hydrocarbon solvents such as toluene, xylene and the like; ester solvents such as ethyl acetate and the like; and ether solvents such as tetrahydrofuran, dioxane, diethyl ether, dimethoxyethane and the like. Of these, particularly preferred are halogenated solvents or aromatic hydrocarbon solvents. The total amount of the solvent used when water is added is preferably from about 1 to 500 mL and more preferably from about 10 to 50 mL, based on 1 mmole of the titanium tetraalkoxide compound. Further, when an inorganic salt containing water of crystallization is used, for example, hydrates such as $Na_2B_4O_7 \cdot 10H_2O$, $Na_2SO_4 \cdot 10H_2O$, $Na_3PO_4 \cdot 12H_2O$, $MgSO_4 \cdot 7H_2O$, $CuSO_4 \cdot 5H_2O$, $FeSO_4 \cdot 7H_2O$, $AlNa(SO_4)_2 \cdot 12H_2O$, $AlK(SO_4)_2 \cdot 12H_2O$ and the like can be used, though examples are not limited thereto. When a moisture-absorbed molecular sieve is used, commercial products such as molecular sieves 3A, 4A and the like exposed to outdoor air may be used, and any of a powder molecular sieve and a pellet molecular sieve can be used. Further, when an inorganic salt containing water of crystallization or a molecular sieve is used, it can be easily removed by filtering before it is reacted with a ligand.

The reaction of the titanium tetraalkoxide compound with water is preferably carried out at a temperature which does not freeze the solvent. Usually, the reaction is carried out at about room temperature, for example, from 15 to 30 degree centigrade. The reaction may be carried out by heating depending on the boiling point of the solvent in use.

The time required for the reaction is different depending on general conditions such as the amount of water to be added, the reaction temperature and the like. For example, when the reaction is carried out at 25 degree centigrade using aqueous dichloromethane prepared by saturating water in dichloromethane, and the amount of water is 0.5 mole based on 1 mole of the titanium tetraalkoxide compound, the time required for stirring is preferably about 18 hours because much higher enantioselectivity is exhibited in the asymmetric cyanation reaction. When the amount of water is 0.75 mole based on 1 mole of the titanium tetraalkoxide compound at 25 degree centigrade, the reaction can be carried out by stirring for about 2 hours.

Next, to a reaction mixture of the titanium tetraalkoxide compound with water obtained as above is added an optically active ligand. The content of the optically active ligand is preferably from 0.1 to 3.0 moles and more preferably from 0.3 to 2.0 moles, based on 1 mole of titanium, and the optically active ligand in that amount is added and stirred. Further, the optically active ligand may be dissolved in a solvent or may be added as it is without being dissolved. When a solvent is used, the solvent can be the same solvent as or different from the solvent used in the above step of adding water. When a solvent is newly added, the amount thereof is from about 1 to 5,000 mL and preferably from about 10 to 500 mL, based on 1 mmole of the titanium atom. At this time, the reaction temperature is not particularly limited, but the compound can be usually produced by stirring at about room temperature, for example, from 15 to 30 degree centigrade for about 5 minutes to 1 hour.

The production of the titanium compound of the present invention is preferably carried out under a dry inert gas atmosphere. Examples of the inert gas include nitrogen, argon, helium and the like.

[Production from a Titanium Oxoalkoxide Compound Represented by the General Formula (a)]

The titanium compound of the present invention can also be produced by mixing the titanium oxoalkoxide compound represented by the above general formula (a) with the optically active ligand represented by the above general formula (b) or (c).

The optically active ligand is preferably added in an amount of from 0.1 to 3.0 moles and more preferably from 0.3 to 2.0 moles, based on 1 mole of the titanium atom in the titanium oxoalkoxide compound, followed by stirring, whereby the titanium compound of the present invention is obtained. At that time, in order to smoothly progress the reaction, a solvent is preferably used. It is preferable that the solvent in use dissolves any one of the titanium oxoalkoxide compound or optically active ligand, or both of them to smoothly progress the reaction. Examples of the solvent include halogenated hydrocarbon solvents such as dichloromethane, chloroform and the like; halogenated aromatic hydrocarbon solvents such as fluorobenzene, trifluoromethylbenzene and the like; aromatic hydrocarbon solvents such as toluene, xylene and the like; ester solvents such as ethyl acetate and the like; and ether solvents such as tetrahydrofuran, dioxane, diethyl ether, dimethoxyethane and the like. Of these, particularly preferred are halogen solvents or aromatic hydrocarbon solvents.

The total amount of the solvent used is preferably from about 1 to 5,000 mL and more preferably from about 10 to 500 mL, based on 1 mmole of the titanium atom in the titanium oxoalkoxide compound. The temperature at this time is not particularly limited, but the reaction can be usually carried out at about room temperature, for example, from 15 to 30 degree centigrade. The time required for preparing a catalyst is preferably from about 5 minutes to 1 hour at about room temperature.

[Alcohol]

Meanwhile, when a catalyst is prepared by mixing the titanium oxoalkoxide compound with the optically active ligand in a solvent, alcohols can also be added. Examples of the alcohols to be added at this time include an aliphatic alcohol and an aromatic alcohol, each of which may have a substituent, and one kind or two or more kinds may be mixed, prior to use.

As the aliphatic alcohol, preferred is a linear, branched or cyclic alkyl alcohol having not more than 10 carbon atoms, and examples thereof include methanol, ethanol, n-propanol, isopropanol, n-butanol, sec-butanol, tert-butanol, cyclopentyl alcohol, cyclohexyl alcohol and the like.

The aforementioned linear, branched or cyclic alkyl alcohol may have, as a substituent on the alkyl group, a halogen atom such as a fluorine atom, a chlorine atom, a bromine atom, an iodine atom and the like.

Examples of the alkyl alcohol having a halogen atom include halogenated alkyl alcohols having not more than 10 carbon atoms such as chloromethanol, 2-chloroethanol, trifluoromethanol, 2,2,2-trifluoroethanol, perfluoroethanol, perfluorohexyl alcohol and the like.

As the aromatic alcohol, preferred is an aryl alcohol having 6 to 20 carbon atoms, and examples thereof include phenol, naphthol and the like.

The aforementioned aryl alcohol may have, as a substituent on the aryl group, a halogen atom such as a fluorine atom, a chlorine atom, a bromine atom, an iodine atom and the like, or an alkyl group having not more than 20 carbon atoms.

Examples of the aryl alcohol having a halogen atom include halogenated aryl alcohols having 6 to 20 carbon atoms such as pentafluorophenol and the like.

Examples of the aryl alcohol having an alkyl group include dimethylphenol, trimethylphenol, isopropylphenol, diisopropylphenol, tert-butylphenol, di-tert-butylphenol and the like.

When a catalyst is prepared by adding these alcohols, the amount thereof is from 0.5 to 20 moles and preferably from 1 to 10 moles, based on 1 mole of the titanium atom of the above titanium compound. Further, these alcohols are preferably added at the time of producing the aforementioned titanium compound. Due to this, in the asymmetric cyanation reaction, high reactivity and high optical yield can be obtained with good reproducibility.

The titanium compound produced as above can be used for the asymmetric catalytic reaction as it is without carrying out a special purification operation. In particular, the compound is suitable for the asymmetric cyanation reaction of aldehyde or unsymmetrical ketone that is the method of the present invention.

[Process for Producing Optically Active Cyanohydrins]

A process for producing optically active cyanohydrins will be described below.

In the method of the present invention, aldehyde or ketone to be used as a starting material is not particularly limited as far as it is a prochiral compound having a carbonyl group in a molecule, and can be suitably selected corresponding to the desired optically active cyanohydrins.

The process of the present invention is particularly suitable when corresponding optically active cyanohydrins is produced from a carbonyl compound represented by the general formula (d) as a starting material.

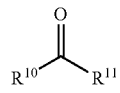

(d)

In the above general formula (d), $R^{10}$ and $R^{11}$ are different groups, and each represent a hydrogen atom, an alkyl group, an alkenyl group, an alkynyl group, an aryl group, an aromatic heterocyclic group or a non-aromatic heterocyclic group, each of which may have a substituent. Furthermore, $R^{10}$ and $R^{11}$ may be linked together to form a ring.

As the alkyl group in $R^{10}$ and $R^{11}$, preferred is a linear, branched or cyclic alkyl group having not more than 20 carbon atoms, and concrete examples thereof include a methyl group, an ethyl group, an n-propyl group, an isopropyl group, an n-butyl group, an isobutyl group, a sec-butyl group, a tert-butyl group, a cyclopentyl group, a cyclohexyl group and the like.

The aforementioned linear, branched or cyclic alkyl group may have, as a substituent, a halogen atom, an aryl group having not more than 20 carbon atoms, an aromatic heterocyclic group having not more than 20 carbon atoms, a non-aromatic heterocyclic group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the alkyl group having a halogen atom include a chloromethyl group, a 2-chloroethyl group, a trifluoromethyl group, a 2,2,2-trifluoroethyl group, a perfluoroethyl group, a perfluorohexyl group and the like.

Examples of the alkyl group having an aryl group include substituted or unsubstituted aralkyl groups such as a benzyl group, a 4-methoxybenzyl group, a 2-phenylethyl group, a cumyl group, an α-naphthylmethyl group, a trityl group and the like.

Examples of the alkyl group having an aromatic heterocyclic group include a 2-pyridylmethyl group, a furfuryl group, a 2-thienylmethyl group and the like.

Examples of the alkyl group having a non-aromatic heterocyclic group include a tetrahydrofurfuryl group and the like.

Examples of the alkyl group having an oxygen-containing group include a methoxyethyl group, a phenoxyethyl group and the like.

Examples of the alkyl group having a nitrogen-containing group include a 2-(dimethylamino)ethyl group, a 3-(diphenylamino)propyl and the like.

Examples of the alkyl group having a silicon-containing group include a 2-(trimethylsiloxy)ethyl group and the like.

As the alkenyl group in $R^{10}$ and $R^{11}$, preferred is a linear, branched or cyclic alkenyl group having 2 to 20 carbon atoms, and concrete examples thereof include a vinyl group, an allyl group, an isopropenyl group, a crotyl group, a cyclohexenyl group and the like.

The aforementioned linear, branched or cyclic alkenyl group may have, as a substituent, a halogen atom, an aryl group having not more than 20 carbon atoms, an aromatic heterocyclic group having not more than 20 carbon atoms, a non-aromatic heterocyclic group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the alkenyl group having a halogen atom include halogenated alkenyl groups having 2 to 20 carbon atoms such as a 2-chlorovinyl group, a 2,2-dichlorovinyl group, a 3-chloroisopropenyl group and the like.

Examples of the alkenyl group having an aryl group include substituted or unsubstituted aralkenyl groups such as a 2-phenylethenyl group; a 3-phenyl-2-propenyl group and the like.

Examples of the alkenyl group having an aromatic heterocyclic group include a 2-(2-pyridyl)ethenyl group and the like.

Examples of the alkenyl group having a non-aromatic heterocyclic group include a 2-(2-tetrahydrofuryl)ethenyl group and the like.

Examples of the alkenyl group having an oxygen-containing group include a 2-methoxyethenyl group, a 2-phenoxyethenyl group and the like.

Examples of the alkenyl group having a nitrogen-containing group include a 2-(dimethylamino)ethenyl group, a 3-(diphenylamino)propenyl group and the like.

Examples of the alkenyl group having a silicon-containing group include a 2-(trimethylsiloxy)ethenyl group and the like.

As the alkynyl group in $R^{10}$ and $R^{11}$, preferred is an alkynyl group having 2 to 20 carbon atoms, and concrete examples thereof include an ethynyl group, a 1-propynyl group, a 2-propynyl group, a 1-butynyl group, a 1-pentynyl group and the like.

The aforementioned alkynyl group may have, as a substituent, a halogen atom, an aryl group having not more than 20 carbon atoms, an aromatic heterocyclic group having not more than 20 carbon atoms, a non-aromatic heterocyclic group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the alkynyl group having a halogen atom include halogenated alkynyl groups having 2 to 20 carbon atoms such as a 3-chloro-1-propynyl group and the like.

Examples of the alkynyl group having an aryl group include substituted or unsubstituted aralkynyl groups such as a 2-phenylethynyl group, a 3-phenyl-2-propynyl group and the like.

Examples of the alkynyl group having an aromatic heterocyclic group include a 2-(2-pyridylethynyl) group and the like. Examples of the alkynyl group having a non-aromatic heterocyclic group include a 2-tetrahydrofurylethynyl group and the like.

Examples of the alkynyl group having an oxygen-containing group include a 2-methoxyethynyl group, a 2-phenoxyethynyl group and the like.

Examples of the alkynyl group having a nitrogen-containing group include a 2-(dimethylamino)ethynyl group, a 3-(diphenylamino)propynyl group and the like.

Examples of the alkynyl group having a silicon-containing group include a 2-(trimethylsiloxy)ethynyl group and the like.

As the aryl group in $R^{10}$ and $R^{11}$, preferred is an aryl group having 6 to 20 carbon atoms, and concrete examples thereof include a phenyl group, a naphthyl group, a biphenyl group, an anthryl group and the like.

The aforementioned aryl group may have, as a substituent, a halogen atom, an alkyl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the halogen atom include a fluorine atom, a chlorine atom, a bromine atom, an iodine atom and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the aryl group having a halogen atom include a 4-fluorophenyl group, a pentafluorophenyl group and the like.

Examples of the aryl group having an alkyl group include a tolyl group, a 3,5-dimethylphenyl group, a 2,4,6-trimethylphenyl group, a 4-isopropylphenyl group, a 3,5-diisopropylphenyl group, a 4-tert-butylphenyl group, a 2,6-di-tert-butylphenyl group and the like.

Examples of the aryl group having an oxygen-containing group include an alkoxy-substituted aryl group such as a 4-methoxyphenyl group, a 3,5-dimethoxyphenyl group, a 3,5-diisopropoxyphenyl group, a 2,4,6-triisopropoxyphenyl group and the like; and an aryloxy-substituted aryl group such as a 2,6-diphenoxyphenyl group and the like.

Examples of the aryl group having a nitrogen-containing group include a 4-(dimethylamino)phenyl group, a 4-nitrophenyl group and the like. Examples of the aryl group having a silicon-containing group include a 3,5-bis(trimethylsilyl)phenyl group, a 3,5-bis(trimethylsiloxy)phenyl group and the like.

As the aromatic heterocyclic group in $R^{10}$ and $R^{11}$, preferred is an aromatic heterocyclic group having 3 to 20 carbon atoms, and concrete examples thereof include an imidazolyl group, a furyl group, a thienyl group, a pyridyl group and the like.

The aforementioned aromatic heterocyclic group may have an alkyl group having not more than 20 carbon atoms, an oxygen-containing group having not more than 20 carbon atoms, a nitrogen-containing group having not more than 20 carbon atoms, a silicon-containing group having not more than 20 carbon atoms or the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like. Examples of the silicon-containing group having not more than 20 carbon atoms include those having not more than 20 carbon atoms such as a silyl group, a silyloxy group and the like.

Examples of the aromatic heterocyclic group having an alkyl group include an N-methylimidazolyl group, a 4,5-dimethyl-2-furyl group and the like.

Examples of the aromatic heterocyclic group having an oxygen-containing group include a 5-butoxycarbonyl-2-furyl group and the like.

Examples of the aromatic heterocyclic group having a nitrogen-containing group include a 5-butylaminocarbonyl-2-furyl group and the like.

As the non-aromatic heterocyclic group in $R^{10}$ and $R^{11}$, preferred is a non-aromatic heterocyclic group having 4 to 20 carbon atoms, and concrete examples thereof include a pyrrolidyl group, a piperidyl group, a tetrahydrofuryl group and the like.

The aforementioned non-aromatic heterocyclic group may be substituted with an alkyl group having not more than 20 carbon atoms, an aryl group having not more than 20 carbon atoms, an oxygen-containing group having not more than 20 carbon atoms, a nitrogen-containing group having not more than 20 carbon atoms, a silicon-containing group having not more than 20 carbon atoms and the like.

Examples of the oxygen-containing group having not more than 20 carbon atoms include those having not more than 20 carbon atoms such as an alkoxy group, an aryloxy group, an alkoxycarbonyl group, an aryloxycarbonyl group, an acyloxy group and the like.

Examples of the nitrogen-containing group having not more than 20 carbon atoms include an amino group having not more than 20 carbon atoms, an amide group having not more than 20 carbon atoms, a nitro group, a cyano group and the like.

Examples of the silicon-containing group having not more than 20 carbon atoms include those having not more than 20 carbon atoms such as a silyl group, a silyloxy group and the like.

Examples of the non-aromatic heterocyclic group having an alkyl group include a 3-methyl-2-tetrahydrofuranyl group and the like.

Examples of the non-aromatic heterocyclic group having an aryl group include an N-phenyl-4-piperidyl group and the like.

Examples of the non-aromatic heterocyclic group having an oxygen-containing group include a 3-methoxy-2-pyrrolidyl group and the like.

Typical examples of aldehyde which can be used as a starting material in the method of the present invention include propionaldehyde, butylaldehyde, valeraldehyde, isovaleraldehyde, hexaaldehyde, heptaldehyde, octylaldehyde, nonylaldehyde, decylaldehyde, isobutylaldehyde, 2-methylbutylaldehyde, 2-ethylbutylaldehyde, 2-ethylhexanal, pivalaldehyde, 2,2-dimethylpentanal, cyclopropanecarboaldehyde, cyclohexanecarboaldehyde, phenylacetaldehyde, (4-methoxyphenyl)acetaldehyde, 3-phenylpropionaldehyde, benzyloxyacetaldehyde, crotonaldehyde, 3-methylcrotonaldehyde, methacrolein, trans-2-hexenal, trans-cinnamaldehyde, benzaldehyde, o-, m- or p-tolylaldehyde, 2,4,6-trimethylbenzaldehyde, 4-biphenylcarboaldehyde, o-, m- or p-fluorobenzaldehyde, o-, m- or p-chlorobenzaldehyde, o-, m- or p-bromobenzaldehyde, 2,3-, 2,4- or 3,4-dichlorobenzaldehyde, 4-(trifluoromethyl)benzaldehyde, 3- or 4-hydroxybenzaldehyde, 3,4-dihydroxybenzaldehyde, o-, m- or p-anisaldehyde, 3,4-dimethoxybenzaldehyde, 3,4-(methylenedioxy)benzaldehyde, m- or p-phenoxybenzaldehyde, m- or p-benzyloxybenzaldehyde, 2,2-dimethylchromane-6-carboaldehyde, 1- or 2-naphthaldehyde, 2- or 3-furancarboaldehyde, 2- or 3-thiophenecarboaldehyde, 1-benzothiophene-3-carboaldehyde, N-methylpyrrole-2-carboaldehyde, 1-methylindole-3-carboaldehyde, 2-, 3- or 4-pyridinecarboaldehyde and the like.

Furthermore, typical examples of ketone which can be used as a starting material in the method of the present invention include 2-butanone, 2-pentanone, 2-hexanone, 2-heptanone, 2-octanone, isopropylmethyl ketone, cyclopentylmethyl ketone, cyclohexylmethyl ketone, phenylacetone, p-methoxyphenylacetone, 4-phenylbutan-2-on, cyclohexylbenzyl ketone, acetophenone, o-, m- or p-methylacetophenone, 4-acetylbiphenyl, o-, m- or p-fluoroacetophenone, o-, m- or p-chloroacetophenone, o-, m- or p-bromoacetophenone, 2',3'-, 2',4'- or 3',4'-dichloroacetophenone, m- or p-hydroxyacetophenone, 3',4'-dihydroxyacetophenone, o-, m- or p-methoxyacetophenone, 3',4'-dimethoxyacetophenone, m- or p-phenoxyacetophenone, 3',4'-diphenoxyacetophenone, m- or p-benzyloxyacetophenone, 3',4'-dibenzyloxyacetophenone, 2-chloroacetophenone, 2-bromoacetophenone, propiophenone, 2-methylpropiophenone, 3-chloropropiophenone, butyrophenone, phenylcyclopropyl ketone, phenylcyclobutyl ketone, phenylcyclopentyl ketone, phenylcyclohexyl ketone, 1- or 2-acenaphthone, chalcone, 1-indanone, 1- or 2-tetralone, 4-chromanone, trans-4-phenyl-3-buten-2-on, 2- or 3-acetylfuran, 2- or 3-acetylthiophene, 2-, 3- or 4-acetylpyridine and the like.

[Cyanating Agent]

In the method of the present invention, a cyanating agent is preferably at least one kind selected from hydrogen cyamide, trialkylsilyl cyamide, acetone cyanohydrin, cyanoformate ester, potassium cyamide-acetic acid and potassium cyamide-acetic anhydride.

The cyanating agent is preferably used in an amount of from 1 to 3 moles and more preferably from 1.05 to 2 moles, based on 1 mole of aldehyde or ketone.

Furthermore, the amount of the aforementioned titanium compound to be used in the method of the present invention is from 0.01 to 30 mole % and preferably from 0.05 to 5.0 mole % based on 1 mole of aldehyde or ketone in terms of the titanium atom, and is identically from 0.01 to 30 mole % and preferably from 0.05 to 5.0 mole % in terms of the optically active ligand.

In the method of the present invention, it is preferable to use a solvent. Preferable examples of the solvent in use include halogenated hydrocarbon solvents such as dichloromethane, chloroform and the like; halogenated aromatic hydrocarbon solvents such as chlorobenzene, o-dichlorobenzene, fluorobenzene, trifluoromethylbenzene and the like; aromatic hydrocarbon solvents such as toluene, xylene and the like; ester solvents such as ethyl acetate and the like; and ether solvents such as tetrahydrofuran, dioxane, diethyl ether, dimethoxyethane, cyclopentylmethyl ether and the like. Of these, particularly preferred are halogenated hydrocarbon solvents or aromatic hydrocarbon solvents. Furthermore, these solvents can be used singly or in combination as a mixed solvent. The total amount of the solvent used is preferably from about 0.1 to 5 mL and more preferably from about 0.2 to 1 mL, based on 1 mmole of aldehyde or ketone as a substrate.

The reaction of the present invention can be carried out by adding an appropriate solvent to a solution of the titanium compound produced according to the present invention, stirring the mixture at room temperature for about 30 minutes, and then adding aldehyde as a substrate and a cyanating agent in order, and stirring the resulting solution at about −5 to 30 degree centigrade for about 30 minutes to 4 hours for the reaction. When ketone is used as a substrate, the reaction can be carried out in the same order. However, in order to complete the reaction, it is preferable to stir the resulting solution for 4 to 36 hours. In case of using a ketone, it need a long time for the reaction. Therefore, it is preferable to add a titanium catalyst one by one for maintaining the reaction speed and optical yield.

When trimethylsilyl cyamide is used as a cyanating agent, the optically active cyanohydrins can be isolated as cyanohydrin trimethylsilyl ether after the completion of the reaction. However, cyanohydrin trimethylsilyl ether is treated with an acid such as dilute hydrochloric acid or the like, and then extracted by a solvent. Then, the solvent is removed under a reduced pressure. Subsequently, the resulting solution was separated according to the usual method such as recrystallization, silica gel column chromatography, distillation or the like. Thereby, the desired optically active cyanohydrin can be isolated. In addition, if the crude product is hydrolyzed, a cyano group can be converted into a carboxylic acid. So, such a method is also useful as a process for producing an optically active hydroxycarboxylic acid.

EXAMPLES

The present invention is now more specifically illustrated below with reference to Examples. However, the present invention is not restricted to these Examples.

ZMD4000 (a product of Waters Corporation) was used for the mass spectrometry (ESI-MS measurement) of a reaction mixture of titanium tetraalkoxide with water, and titanium oxoalkoxide. The content of titanium was measured according to the ICP atomic emission spectrometry (a product of Seiko Instrument Inc., SPS1200A). The product of the asymmetric cyanation reaction was identified by $^1$H NMR measurement result (a product of JEOL Ltd., JEOL-GSX-270) and comparison between the already reported value of the optical rotation and actual measurement value (a product of JASCO Corporation, DIP-370) data. The conversion and optical yield of the asymmetric cyanation reaction were measured by using gas chromatography (products of Shimadzu Corporation, GC-14A and GC-17). At this time, CHIRAL- DEX G-TA (a product of Advanced Separation Technologies, Inc.) was used as a chiral column. The absolute configuration of the product was determined by comparing the optical rotation to the already reported value. MKC-210 (a product of Kyoto Electronics Manufacturing Co., Ltd.) was used for the measurement of the moisture content in a solvent. The moisture content of a molecular sieve was obtained from the weight loss up to 400 degree centigrade by using TG8120 (a product of Rigaku Inc.) for carrying out a thermogravimetric analysis. UV-2500PC (a product of Shimadzu Corporation) was used for the measurement of ultraviolet visible (UV-VIS) absorbance.

Dichloromethane for organic synthesis (hereinafter referred to as "dehydrated dichloromethane") (manufactured by Kanto Chemical Co., Inc.) was used for the production of titanium oxoalkoxide, the preparation of a ligand solution and the reaction. Organic synthesis grade reagents (products of Kanto Chemical Co., Inc.) were used without further purification for titanium tetra-n-butoxide and titanium tetraisopropoxide. As titanium tetraethoxide, a product of Merck Ltd. was used as it was. Commercial products were used as they were without further purification for aldehydes and ketones employed as substrates. A product of Matsumoto Chemical Industry Co., Ltd. was used as it was for a titanium butoxide dimer. A product of Acros Organics was used as it was without purification for trimethylsilyl cyamide of a cyanating agent. The optically active ligand was produced in accordance with the already reported method and used by degassing and drying just prior to use. Commercial products were used as they were without further purification for inorganic salts containing water of crystallization. A product in a form of powder manufactured by Aldrich having a particle diameter of not more than 5 μm was used for molecular sieves 4A.

All of the reactions were carried out under a nitrogen atmosphere. Apparatus used for the reaction was all washed with dilute nitric acid and then sufficiently dried, prior to use.

Reference Example 1

Synthesis of a Titanium Oxoethoxide Compound $(Ti_7O_4)(OEt)_{20}$

In a 100-ml, 3-necked flask, 11.4 g (0.050 mole) of titanium tetraethoxide was weighed and dissolved with 35 mL of dehydrated ethanol to obtain a colorless clear solution. A solution with 0.45 g (0.025 mole) of water dissolved in 15 mL of dehydrated ethanol was added dropwise thereto using a dropping funnel over 15 minutes. The solution was slowly whitened to give a white suspension. After the dropwise addition was completed, the resulting suspension was stirred at room temperature for 1 hour and then a precipitate was obtained by filtering under nitrogen flow. The obtained white precipitate washed with anhydrous ethanol and then dried in vacuo to obtain white powder. The content of titanium was 25.6%. Since the theoretical content of titanium in the titanium oxoalkoxide compound $(Ti_7O_4)(OEt)_{20}$ was 25.77%, the obtained white powder was determined as a titanium oxoalkoxide compound $(Ti_7O_4)(OEt)_{20}$ as described in J. Am. Chem. Soc., Vol. 113, p. 8190 (1991). The quantity was 6.68 g and the yield was 72%. The obtained white powder was dissolved in dichloromethane or n-hexane to give a colorless clear solution, and no insoluble substances were found to these solvents. The ESI-MS measurement was carried out, and as a result, m/z 1341 was observed.

Preparation Example 1

Preparation of a Solution of a Partial Hydrolysate of Titanium tetra-n-butoxide (Reaction of Titanium Tetraalkoxide with Water)

To a 200 mL separatory funnel were added 150 mL of dichloromethane and 5 mL of distilled water. The resulting material was shaken and allowed to stand until the mixture was separated into two layers, and then a lower layer (dichloromethane layer) was taken out. The dichloromethane was further filtered by using a separatory filter paper (a product of Toyo Roshi Kaisha, Ltd.) to obtain aqueous dichloromethane (moisture content: 1,302 ppm). In a 100 mL volumetric flask was weighed 1.70 g (5.00 mmole) of titanium tetra-n-butoxide. 40 mL of dehydrated dichloromethane was added thereto to dissolve titanium tetra-n-butoxide, and then 39.1 mL of aqueous dichloromethane (moisture content: 3.75 mmole; 0.75 mole based on 1 mole of titanium) was added and subsequently diluted with dehydrated dichloromethane. The solution was moved to a lid-attached vessel and stirred at room temperature for 18 hours to obtain a uniform, colorless clear solution of a partial hydrolysate of titanium tetra-n-butoxide. The ESI-MS measurement of this solution was carried out, and as a result, m/z 2005 and 1666 were observed.

Preparation Example 2

The same operation as in Preparation Example 1 was carried out except that aqueous dichloromethane was added in the amount equivalent to 0.67 mole of the moisture content based on 1 mole of titanium (said to be equivalent to 0.67 mole based on 1 mole of titanium; hereinafter the same), to obtain a uniform, colorless clear solution of a partial hydrolysate of titanium tetra-n-butoxide. The ESI-MS measurement of this solution was carried out, and as a result, m/z 1665 and 1325 were observed.

Preparation Example 3

The same operation as in Preparation Example 1 was carried out except that aqueous dichloromethane was added in the amount equivalent to 0.50 mole based on 1 mole of titanium, to obtain a uniform, colorless clear solution of a partial hydrolysate of titanium tetra-n-butoxide.

Preparation Example 4

The same operation as in Preparation Example 1 was carried out except that aqueous dichloromethane was added in the amount equivalent to 1.0 mole based on 1 mole of titanium, to obtain a uniform, colorless clear solution of a partial hydrolysate of titanium tetra-n-butoxide.

Preparation Example 5

The same operation as in Preparation Example 1 was carried out except that stirring time required for hydrolysis was set to 2 hours instead of stirring at room temperature for 18 hours, to obtain a uniform, colorless clear solution of a partial hydrolysate of titanium tetra-n-butoxide.

Preparation Example 6

In a 20 mL sample bottle, 0.0191 g (0.0500 mmole; equivalent to 1.00 mole of water based on 1 mole of titanium) of $Na_2B_4O_7 \cdot 10H_2O$ was weighed, and 0.17 g (0.50 mmole) of titanium tetra-n-butoxide and 3 mL of dehydrated dichloromethane were added thereto. The lid was tightly sealed, and the resulting material was stirred at room temperature for 18 hours and then filtered by using a membrane filter having a pore diameter of 0.2 μm. The filtrate was moved to a 10 mL volumetric flask and dehydrated dichloromethane was added thereto for diluting the solution to give 10 mL, to obtain a uniform, colorless clear solution of a partial hydrolysate of titanium tetra-n-butoxide.

Preparation Example 7

The same operation as in Preparation Example 6 was carried out except that deuterated chloroform was used as a solvent instead of dichloromethane, to obtain a uniform, colorless clear solution of a partial hydrolysate of titanium tetra-n-butoxide. This solution was analyzed by $^1H$ NMR and the results thereof are shown in FIG. 1. The peak derived from proton of a methylene group in a position adjacent to oxygen of butoxide was observed near 4.3 ppm before the hydrolysis, whereas the peak in a broad range of from 4.1 to 4.6 ppm was observed after the hydrolysis operation. Furthermore, the peak of butanol was observed near 3.7 ppm.

Preparation Example 8

The same operation as in Preparation Example 6 was carried out except that the amount of $Na_2B_4O_7 \cdot 10H_2O$ added was changed to 0.0238 g (0.0625 mmole; equivalent to 1.25 mole of water based on 1 mole of titanium), to obtain a uniform, colorless clear solution of a partial hydrolysate of titanium tetra-n-butoxide.

Preparation Example 91

The same operation as in Preparation Example 6 was carried out except that 0.0161 g (0.0500 mmole; equivalent to 1.00 mole of water based on 1 mole of titanium) of $Na_2SO_4 \cdot 10H_2O$ was used instead of $Na_2B_4O_7 \cdot 10H_2O$, to obtain a uniform, colorless clear solution of a partial hydrolysate of titanium tetra-n-butoxide.

Preparation Example 10

The same operation as in Preparation Example 6 was carried out except that 0.0176 g (0.0714 mmole; equivalent to 1.00 mole of water based on 1 mole of titanium) of $MgSO_4 \cdot 7H_2O$ was used instead of $Na_2B_4O_7 \cdot 10H_2O$, to obtain a uniform, colorless clear solution of a partial hydrolysate of titanium tetra-n-butoxide.

Preparation Example 11

On a 12 cm magnetic plate, 50 g of a powder molecular sieve 4A was weighed, coated with paper and then allowed to stand in a laboratory. A change in the weight was observed and as a result, the weight was slowly increased and reached almost constant weight for 4 days. This was used as a moisture-absorbent powder of molecular sieve 4A and moved to a glass sample bottle, and the resultant was tightly sealed. The amount of moisture was measured, and as a result, it was 19.2%. In a 20 mL sample bottle was weighed 0.0469 g (equivalent to 1.00 mole of water based on 1 mole of titanium) of the moisture-absorbent powder of molecular sieve 4A (moisture content: 19.2%), and 0.17 g (0.50 mmole) of titanium tetra-n-butoxide and 3 mL of dehydrated dichloromethane were added thereto. The lid was covered and tightly sealed. The resulting material was stirred at room temperature for 18 hours and then filtered by using a membrane filter having a pore diameter of 0.2 μm. The filtrate was moved to a 10 mL volumetric flask, dehydrated dichloromethane was added thereto for diluting the solution to give 10 mL, to obtain a uniform, colorless clear solution of a partial hydrolysate of titanium tetra-n-butoxide.

Preparation Example 12

The same operation as in Preparation Example 11 was carried out except that the amount of the moisture-absorbent powder of molecular sieve 4A (moisture content: 19.2%) added was changed to 0.0586 g (equivalent to 1.25 mole of water based on 1 mole of titanium), to obtain a uniform, colorless clear solution of a partial hydrolysate of titanium tetra-n-butoxide.

Preparation Example 13

The same operation as in Preparation Example 11 was carried out except that the amount of the moisture-absorbent powder of molecular sieve 4A (moisture content: 19.2%) was changed to 0.0352 g (equivalent to 0.75 mole of water based on 1 mole of titanium), to obtain a uniform, colorless clear solution of a partial hydrolysate of titanium tetra-n-butoxide.

Preparation Example 14

The same operation as in Preparation Example 1 was carried out except that titanium tetraethoxide was used instead of titanium tetra-n-butoxide, to obtain a uniform, colorless clear solution of a partial hydrolysate of titanium tetraethoxide. The ESI-MS measurement of this solution was carried out, and as a result, m/z 1341 was observed.

Preparation Example 15

Preparation of a Titanium Oxoethoxide Solution 93 mg (0.5 mmole in terms of titanium) of titanium oxoethoxide obtained in Reference Example 1 was weighed in a 10 mL volumetric flask and diluted with dehydrated dichloromethane. At this time, 115 mg (2.5 mmole) of dehydrated ethanol was added thereto. The resulting material was fully shaken to obtain a uniform, colorless clear solution of titanium oxoethoxide.

Preparation Example 16

138 mg (0.5 mmole in terms of titanium) of a commercial titanium butoxide dimer was weighed in a 10 mL volumetric flask and diluted with dehydrated dichloromethane. At this time, 371 mg (2.5 mmole) of dehydrated butanol was added thereto. The resulting material was fully shaken to obtain a uniform, colorless clear solution of titanium oxo-n-butoxide.

Example 1

Production of a Titanium Compound (Catalyst)

In a 1 mL volumetric flask was weighed 0.10 mL (0.0050 mmole in terms of titanium) of the solution of a partial hydrolysate of titanium tetra-n-butoxide obtained in Preparation Example 1. Subsequently, 0.50 mL (0.0050 mmole) of a dichloromethane solution (0.01 mole/L) of (S)-2-(N-3,5-ditert-butylsalicylidene)amino-3-methyl-1-butanol (above formula (c-8)) was added thereto and diluted with a dehydrated dichloromethane solution, and then the resulting material was stirred at room temperature for 30 minutes to obtain a catalyst solution.

Asymmetric Cyanation Reaction 0.20 mL (0.001 mmole as titanium; equivalent to 0.2 mole % based on the substrate) of this catalyst solution was weighed in a test tube, and 57 mg (0.50 mmole) of heptaldehyde and 74 mg (0.75 mmole) of trimethylsilyl cyamide were added in order. The resulting material was stirred at room temperature for 30 minutes for the reaction and the GC analysis was carried out. As a result, the conversion of substrate was not less than 99%, while the optical yield of generated 2-trimethylsiloxy octanenitrile was 88% ee. It was found that (S)-form was mainly obtained.

Example 2

The reaction was carried out in the same manner as in Example 1 except that the solution obtained in Preparation Example 2 was used as a solution of a partial hydrolysate of titanium tetra-n-butoxide. The conversion of substrate was not less than 99%, while the optical yield of generated 2-trimethylsiloxy octanenitrile was 87% ee ((S)-form).

Example 3

The reaction was carried out in the same manner as in Example 1 except that the solution obtained in Preparation Example 3 was used as a solution of a partial hydrolysate of titanium tetra-n-butoxide. The conversion of substrate was 90%, while the optical yield of generated 2-trimethylsiloxy octanenitrile was 88% ee ((S)-form).

Example 4

The reaction was carried out in the same manner as in Example 1 except that the solution obtained in Preparation Example 4 was used as a solution of a partial hydrolysate of titanium tetra-n-butoxide. The conversion of substrate was 99%, while the optical yield of generated 2-trimethylsiloxy octanenitrile was 88% ee ((S)-form).

Example 5

The reaction was carried out in the same manner as in Example 1 except that the solution obtained in Preparation Example 5 was used as a solution of a partial hydrolysate of titanium tetra-n-butoxide. The conversion of substrate was 99%, while the optical yield of generated 2-trimethylsiloxy octanenitrile was 85% ee ((S)-form).

Example 6

The reaction was carried out in the same manner as in Example 1 except that the solution obtained in Preparation Example 6 was used as a solution of a partial hydrolysate of titanium tetra-n-butoxide and the reaction time in the asymmetric cyanation reaction was set to 1 hour. The conversion of substrate was 99%, while the optical yield of generated 2-trimethylsiloxy octanenitrile was 88% ee ((S)-form).

Example 7

A titanium compound (catalyst) was produced in the same manner as in Example 1 except that 0.20 mL (0.010 mmole in terms of titanium; 2 time moles based on the ligand) of the solution obtained in Preparation Example 6 as a solution of a partial hydrolysate of titanium tetra-n-butoxide. This catalyst solution was diluted with dehydrated dichloromethane and the UV-VIS absorbance measurement was carried out. Data on UV-VIS absorption spectrum are shown in FIG. 2. Comparison between the spectrum of the catalyst solution and two spectra of solutions of the raw materials with the same concentration indicated that a new absorption band generated in the wavelength range (370 to 450 nm) where no absorption from the raw material was observed.

The asymmetric cyanation reaction was carried out in the same manner as in Example 1 using the catalyst solution before the dilution. As a result, the conversion of substrate was 99%, while the optical yield of generated 2-trimethylsiloxy octanenitrile was 88% ee ((S)-form).

Example 8

The reaction was carried out in the same manner as in Example 1 except that the solution obtained in Preparation Example 7 was used as a solution of a partial hydrolysate of titanium tetra-n-butoxide and deuterated chloroform was used as a solvent instead of dichloromethane. The conversion of substrate was 99%, while the optical yield of generated 2-trimethylsiloxy octanenitrile was 88% ee ((S)-form).

Example 9

The reaction was carried out in the same manner as in Example 1 except that the solution obtained in Preparation Example 8 was used as a solution of a partial hydrolysate of titanium tetra-n-butoxide and the reaction time in the asymmetric cyanation reaction was set to 1 hour. The conversion of substrate was 99%, while the optical yield of generated 2-trimethylsiloxy octanenitrile was 88% ee ((S)-form).

Example 10

The reaction was carried out in the same manner as in Example 1 except that the solution obtained in Preparation Example 9 was used as a solution of a partial hydrolysate of titanium tetra-n-butoxide and the reaction time in the asymmetric cyanation reaction was set to 1 hour. The conversion of substrate was 98%, while the optical yield of generated 2-trimethylsiloxy octanenitrile was 88% ee ((S)-form).

Example 11

The reaction was carried out in the same manner as in Example 1 except that the solution obtained in Preparation Example 10 was used as a solution of a partial hydrolysate of titanium tetra-n-butoxide and the reaction time in the asymmetric cyanation reaction was set to 1 hour. The conversion of substrate was 86%, while the optical yield of generated 2-trimethylsiloxy octanenitrile was 85% ee ((S)-form).

Example 12

The reaction was carried out in the same manner as in Example 1 except that the solution obtained in Preparation Example 11 was used as a solution of a partial hydrolysate of titanium tetra-n-butoxide and the reaction time in the asymmetric cyanation reaction was set to 1 hour. The conversion of substrate was not less than 99%, while the optical yield of generated 2-trimethylsiloxy octanenitrile was 87% ee ((S)-form).

Example 13

The reaction was carried out in the same manner as in Example 1 except that the solution obtained in Preparation Example 12 was used as a solution of a partial hydrolysate of titanium tetra-n-butoxide and the reaction time in the asymmetric cyanation reaction was set to 1 hour. The conversion of substrate was not less than 99%, while the optical yield of generated 2-trimethylsiloxy octanenitrile was 88% ee ((S)-form).

Example 14

The reaction was carried out in the same manner as in Example 1 except that the solution obtained in Preparation Example 13 was used as a solution of a partial hydrolysate of titanium tetra-n-butoxide and the reaction time in the asymmetric cyanation reaction was set to 1 hour. The conversion of substrate was not less than 99%, while the optical yield of generated 2-trimethylsiloxy octanenitrile was 84% ee ((S)-form).

Example 15

The reaction was carried out in the same manner as in Example 1 except that the solution of a partial hydrolysate of titanium tetraethoxide obtained in Preparation Example 14 was used instead of the solution of a partial hydrolysate of titanium tetra-n-butoxide. The conversion of substrate was 92%, while the optical yield of generated 2-trimethylsiloxy octanenitrile was 83% ee ((S)-form).

Example 16

The reaction was carried out in the same manner as in Example 15 except that the solution of titanium oxoethoxide obtained in Preparation Example 15 was used instead of the solution of a partial hydrolysate of titanium tetraethoxide. The conversion of substrate was 99%, while the optical yield of generated 2-trimethylsiloxy octanenitrile was 84% ee ((S)-form).

Example 17

The reaction was carried out in the same manner as in Example 3 except that (S)-2-(N-3-tert-butylsalicylidene)amino-3-methyl-1-butanol (above formula (c-2)) was used as an optically active ligand and the reaction time in the asymmetric cyanation reaction was set to 2 hours. The conversion of substrate was not less than 99%, while the optical yield of generated 2-trimethylsiloxy octanenitrile was 88% ee ((S)-form).

Example 18

In a test tube was weighed 0.020 mL (0.001 mmole in terms of titanium; equivalent to 0.2 mole % based on the substrate) of the solution of titanium oxo-n-butoxide obtained in Preparation Example 16. Subsequently, 0.010 mL (0.0011 mmole; equivalent to 0.22 mole % based on the substrate) of a dichloromethane solution (0.11 mole/L) of (S)-2-(N-3,5-di-tert-butylsalicylidene)amino-3-methyl-1-butanol (above formula (c-8)) was added and 0.20 mL of a dehydrated dichloromethane solution was added thereto, and then the resulting material was stirred at room temperature for 30 minutes to obtain a catalyst solution. To this catalyst solution were added 57 mg (0.50 mmole) of heptaldehyde and 74 mg (0.75 mmole) of trimethylsilyl cyamide in order. The reaction solution was stirred at room temperature for 1 hour, and then diluted with 2.0 mL of dichloromethane and purified by silica gel column chromatography using dichloromethane as an eluent to obtain 2-trimethylsiloxy octanenitrile as colorless oil. Isolated yield: 92%, optical yield: 87% ee, $^1$H NMR (CDCl$_3$) δ: 0.21 (s, 9H, SiCH$_3$), 0.89 (t, 3H, CH$_2$CH$_3$, J=7.0 Hz), 1.28-1.37 (c, 6H, CH$_2$), 1.45 (m, 2H, CH$_2$), 1.78 (m, 2H, CH$_2$), 4.38 (t, 1H, CHCN, J=6.6 Hz), [α]$^{28}_D$ –42.6° (c 0.968, CHCl$_3$), (S)-form.

Example 19

The reaction was carried out in the same manner as in Example 18 except that (S)-2-(N-3,5-di-tert-butylsalicylidene)amino-3,3-dimethyl-1-butanol (above formula (c-9)) was used as an optically active ligand. Analysis was carried out after 30 minutes from the initiation of stirring in the asymmetric cyanation reaction. As a result, the conversion of substrate was 66%, while the optical yield of generated 2-trimethylsiloxy octanenitrile was 80% ee ((S)-form).

Example 20

The reaction was carried out in the same manner as in Example 18 except that (S)-2-(N-3,5-di-tert-butylsalicylidene)amino-3-methyl-1-pentanol (above formula (c-10)) was used as an optically active ligand. Analysis was carried out after 30 minutes from the initiation of stirring in the asymmetric cyanation reaction. As a result, the conversion of substrate was not less than 99%, while the optical yield of generated 2-trimethylsiloxy octanenitrile was 85% ee ((S)-form).

Example 21

The reaction was carried out in the same manner as in Example 18 except that (S)-2-(N-3,5-di-tert-butylsalicylidene)amino-4-methyl-1-pentanol (above formula (c-11)) was used as an optically active ligand. Analysis was carried out after 30 minutes from the initiation of stirring in the asymmetric cyanation reaction. As a result, the conversion of substrate was 88%, while the optical yield of generated 2-trimethylsiloxy octanenitrile was 79% ee ((S)-form).

Example 22

The reaction was carried out in the same manner as in Example 15 except that (S)-2-(N-1-(3,5-di-tert-butyl-2-hydroxyphenyl)ethylidene)amino-3-methyl-1-butanol (above formula (c-19)) was used as an optically active ligand. Analysis was carried out after 30 minutes from the initiation of stirring in the asymmetric cyanation reaction. As a result, the conversion of substrate was 90%, while the optical yield of generated 2-trimethylsiloxy octanenitrile was 87% ee ((S)-form).

Example 23

In a test tube was weighed 0.010 mL (0.0005 mmole in terms of titanium; equivalent to 0.1 mole % based on the substrate) of the solution of titanium oxo-n-butoxide obtained in Preparation Example 16. Subsequently, 0.005 mL (0.00055 mmole; equivalent to 0.11 mole % based on the substrate) of a dichloromethane solution (0.11 mole/L) of (S)-2-(N-3,5-di-tert-butylsalicylidene)amino-3-methyl-1-butanol (above formula (c-8)) was added and 0.20 mL of a dehydrated dichloromethane solution was added thereto, and then the resulting material was stirred at room temperature for 30 minutes to obtain a catalyst solution. To this catalyst solution were added 57 mg (0.50 mmole) of heptaldehyde and 74 mg (0.75 mmole) of trimethylsilyl cyamide in order. The reaction solution was stirred at room temperature for 1 hour, and then diluted with 2.0 mL of dichloromethane and purified by silica gel column chromatography using dichloromethane as an eluent to obtain 2-trimethylsiloxy octanenitrile as colorless oil. The isolated yield was 92%, while the optical yield was 87% ee ((S)-form).

Example 24

The reaction was carried out in the same manner as in Example 18 except that benzaldehyde was used as aldehyde and the reaction time in the asymmetric cyanation reaction was set to 2 hours, to obtain 2-trimethylsiloxy-2-phenyl acetonitrile as colorless oil. Isolated yield: 85%, optical yield: 92% ee, $^1$H NMR (CDCl$_3$) δ: 0.23 (s, 9H, SiCH$_3$), 5.49 (s, 1H, CHCN), 7.4-7.5 (c, 5H, Ar), $[\alpha]^{28}_D$ −24.0° (c 0.877, CHCl$_3$), (S)-form.

Example 25

The reaction was carried out in the same manner as in Example 1 except that o-fluorobenzaldehyde was used as aldehyde. The reaction solution was stirred at room temperature for 3 hours, and then diluted with 2.0 mL of dichloromethane and purified by silica gel column chromatography using dichloromethane as an eluent to obtain 2-trimethylsiloxy-2-(2'-fluorophenyl)acetonitrile as light yellow oil. Isolated yield: 76%, optical yield: 94% ee, $^1$H NMR (CDCl$_3$) δ: 0.24 (s, 9H, SiCH$_3$), 5.75 (s, 1H, CHCN), 7.10 (m, 1H, Ar), 7.22 (dd, 1H, Ar, J=7.6, 1.2 Hz), 7.39 (m, 1H, Ar), 7.64 (dt, 1H, Ar, J=7.6, 1.8 Hz), $[\alpha]^{29}_D$ −21.9° (c 0.849, CHCl$_3$), (S)-form.

Example 26

The reaction was carried out in the same manner as in Example 18 except that phenyl acetaldehyde was used as aldehyde and the reaction time in the asymmetric cyanation reaction was set to 2 hours, to obtain 2-trimethylsiloxy-3-phenyl propionitrile as slightly yellow oil. Isolated yield: 74%, optical yield: 91% ee, $^1$H NMR (CDCl$_3$) δ: 0.18 (s, 9H, SiCH$_3$), 3.06 (d, 1H, CH$_2$Ph, J=7.3 Hz), 4.49 (t, 1H, CHCN, J=7.3 Hz), 7.2-7.3 (c, 5H, Ar), $[\alpha]^{28}_D$ −23.4° (c 0.809, CHCl$_3$), (S)-form.

Example 27

The reaction was carried out in the same manner as in Example 18 except that 2-ethylbutyl aldehyde was used as aldehyde, to obtain 2-trimethylsiloxy-3-ethyl pentanitrile as colorless oil. Isolated yield: 77%, optical yield: 97% ee, $^1$H NMR (CDCl$_3$) δ: 0.21 (s, 9H, SiCH$_3$), 0.94 (t, 6H, CH$_2$CH$_3$, J=7.0 Hz), 1.35-1.7 (c, 5H, CH$_2$CH$_3$ and CH), 4.40 (d, 1H, CHCN, J=4.6 Hz), $[\alpha]^{28}_D$ −55.0° (c 0.763, CHCl$_3$), (S)-form.

Example 28

The asymmetric cyanation reaction was carried out in the same manner as in Example 1 except that aldehyde as shown in Table 1 was used instead of heptaldehyde. The reaction was completed for 30 minutes to 2 hours. In any of these Examples, a desired product was quantitatively obtained. The optical purity of the obtained product was analyzed, and the results thereof are shown in Table 1.

Example 29

The asymmetric cyanation reaction was carried out in the same manner as in Example 1 except that aldehyde as shown in Table 1 was used instead of heptaldehyde. The reaction was completed for 30 minutes to 2 hours. In any of these Examples, a desired product was quantitatively obtained. The optical purity of the obtained product was analyzed, and the results thereof are shown in Table 1.

Example 30

The asymmetric cyanation reaction was carried out in the same manner as in Example 1 except that aldehyde as shown in Table 1 was used instead of heptaldehyde. The reaction was completed for 30 minutes to 2 hours. In any of these Examples, a desired product was quantitatively obtained. The optical purity of the obtained product was analyzed, and the results thereof are shown in Table 1.

Example 31

The asymmetric cyanation reaction was carried out in the same manner as in Example 1 except that aldehyde as shown in Table 1 was used instead of heptaldehyde. The reaction was completed for 30 minutes to 2 hours. In any of these Examples, a desired product was quantitatively obtained. The optical purity of the obtained product was analyzed, and the results thereof are shown in Table 1.

Example 32

The asymmetric cyanation reaction was carried out in the same manner as in Example 1 except that aldehyde as shown in Table 1 was used instead of heptaldehyde. The reaction was completed for 30 minutes to 2 hours. In any of these Examples, a desired product was quantitatively obtained. The optical purity of the obtained product was analyzed, and the results thereof are shown in Table 1.

Example 33

The asymmetric cyanation reaction was carried out in the same manner as in Example 1 except that aldehyde as shown in Table 1 was used instead of heptaldehyde. The reaction was completed for 30 minutes to 2 hours. In any of these Examples, a desired product was quantitatively obtained. The optical purity of the obtained product was analyzed, and the results thereof are shown in Table 1.

TABLE 1

| Examples | Aldehyde | Optical Purity (% ee) |
|---|---|---|
| 28 | 4-Me-C$_6$H$_4$-CHO | 90 |
| 29 | 4-MeO-C$_6$H$_4$-CHO | 89 |

TABLE 1-continued

| Examples | Aldehyde | Optical Purity (% ee) |
|---|---|---|
| 30 | F₃C-C₆H₄-CHO (para) | 89 |
| 31 | 2-furyl-CHO | 89 |
| 32 | cyclohexyl-CHO | 97 |
| 33 | CH₃CH₂CH=CH-CHO | 73 |

Example 34

The reaction was carried out in the same manner as in Example 18 except that acetophenone was used instead of heptaldehyde and the reaction time was set to 24 hours, to obtain 2-trimethylsiloxy-2-phenyl propionitrile as colorless oil. Isolated yield: 91%, optical yield: 92% ee, $^1$H NMR (CDCl$_3$) δ: 0.18 (s, 9H, SiCH$_3$), 1.86 (s, 1H, CH$_3$), 7.34-7.43 (c, 3H, Ar), 7.51-7.56 (c, 2H, Ar), $[\alpha]^{28}_D$ −22.8° (c 1.002, CHCl$_3$), (S)-form.

Example 35

The reaction was carried out in the same manner as in Example 34 was carried out except that cyclohexylmethyl ketone was used instead of acetophenone, to obtain 2-trimethylsiloxy-2-cyclohexyl propionitrile as colorless oil. Isolated yield: 80%, optical yield: 91% ee, $^1$H NMR (CDCl$_3$) δ: 0.23 (s, 9H, SiCH$_3$), 1.52 (s, 1H, CH$_3$), 1.00-1.31 and 1.45-2.00 (c, 11H, CH and CH$_2$), $[\alpha]^{29}_D$ −15.3° (c 0.901, CHCl$_3$), (S)-form.

Example 36

The asymmetric cyanation reaction was carried out in the same manner as in Example 1 except that ketone as shown in Table 2 was used instead of heptaldehyde. The reaction was completed for 2 to 24 hours. In any of these Examples, a desired product was quantitatively obtained. The optical purity of the obtained product was analyzed, and the results thereof are shown in Table 2.

Example 37

The asymmetric cyanation reaction was carried out in the same manner as in Example 1 except that ketone as shown in Table 2 was used instead of heptaldehyde. The reaction was completed for 2 to 24 hours. In any of these Examples, a desired product was quantitatively obtained. The optical purity of the obtained product was analyzed, and the results thereof are shown in Table 2.

Example 38

The asymmetric cyanation reaction was carried out in the same manner as in Example 1 except that ketone as shown in Table 2 was used instead of heptaldehyde. The reaction was completed for 2 to 24 hours. In any of these Examples, a desired product was quantitatively obtained. The optical purity of the obtained product was analyzed, and the results thereof are shown in Table 2.

TABLE 2

| Examples | Ketone | Optical Purity (% ee) |
|---|---|---|
| 36 | 2'-fluoroacetophenone | 93 |
| 37 | isopropyl methyl ketone (3-methyl-2-butanone) | 86 |
| 38 | PhCH₂CH₂C(O)CH₃ | 70 |

Comparative Example 1

Without Adding Water 284 mg (1.0 mmole) of titanium tetraisopropoxide was weighed in a 10 mL volumetric flask and diluted with dehydrated dichloromethane. The resulting material was fully shaken to obtain a uniform, colorless clear solution of titanium tetraisopropoxide. 1.0 mL (0.1 mmole in terms of titanium; equivalent to 20 mole % based on the substrate) of the obtained solution was weighed in a test tube and subsequently 1.0 mL (0.11 mmole; equivalent to 22 mole % based on the substrate) of a dehydrated dichloromethane solution (0.11 mole/L) of (S)-2-(N-3-tert-butylsalicylidene)amino-3-methyl-1-butanol (above formula (c-2)) was added thereto. The resulting mixture was stirred at room temperature for 1 hour to prepare a catalyst solution. After cooling down the temperature to −30° C., 57 mg (0.50 mmole) of heptaldehyde and 124 mg (1.25 mmole) of trimethylsilyl cyamide were added in order while stirring. The mixture was kept stirring, and as a result, the conversion at the 24th hour reached 96%. The optical yield of generated 2-trimethylsiloxy octanenitrile was 37% ee ((R)-form).

Comparative Example 2

The reaction was carried out in the same manner as in Comparative Example 1 except that benzaldehyde was used as aldehyde. The conversion at the 24th hour reached 94%, while the optical yield of generated 2-trimethylsiloxy-2-phenyl acetonitrile was 62% ee ((R)-form).

Comparative Example 3

The reaction was carried out in the same manner as in Comparative Example 2 except that the reaction temperature was set to room temperature and (S)-2-(N-3,5-di-tert-butyl-salicylidene)amino-3-methyl-1-butanol (above formula (c-8)) was used as an optically active ligand. After 6 hours from the initiation of the reaction, the conversion of the substrate reached not less than 99%. The optical yield of generated 2-trimethylsiloxy-2-phenyl acetonitrile was 4% ee ((R)-form).

Comparative Example 4

Adding Water after Mixing Titanium Tetraalkoxide with an Optically Active Ligand 170 mg (0.50 mmole) of titanium tetra-n-butoxide was weighed in a 10 mL volumetric flask and diluted with dehydrated dichloromethane. The resulting material was fully shaken to obtain a uniform, colorless clear solution of titanium tetra-n-butoxide. 0.10 mL (0.005 mmole in terms of titanium; equivalent to 1 mole % based on the substrate) of the obtained solution was weighed in a 1 mL flask and subsequently 0.5 mL (0.005 mmole; equivalent to 1 mole % based on the substrate) of a dehydrated dichloromethane solution (0.01 mole/L) of (S)-2-(N-3,5-di-tert-butylsalicylidene)amino-3-methyl-1-butanol (above formula (c-8)) was added thereto and diluted with dehydrated dichloromethane. Then, the resulting mixture was stirred at room temperature for 30 minutes to prepare a catalyst solution. To this catalyst solution was added 0.062 mL (moisture content: 0.005 mmole) of aqueous dichloromethane. The reaction solution was stirred at room temperature for 2 hours and then 0.50 mL of this solution was weighed in a test tube. 57 mg (0.50 mmole) of heptaldehyde and 74 mg (0.75 mmole) of trimethylsilyl cyamide were further added in order. The resulting mixture was stirred at room temperature for 30 minutes for the reaction, followed by analysis. As a result, the conversion of substrate was 64%, while the optical yield of generated 2-trimethylsiloxy octanenitrile was 18% ee ((S)-form).

The titanium compound of the present invention and the asymmetric cyanation reaction using the titanium compound of the present invention can be used for the production of the optically active cyanohydrins that are compounds useful in the fields of medicines and agrichemical chemicals, and functional materials.

Figure 1:
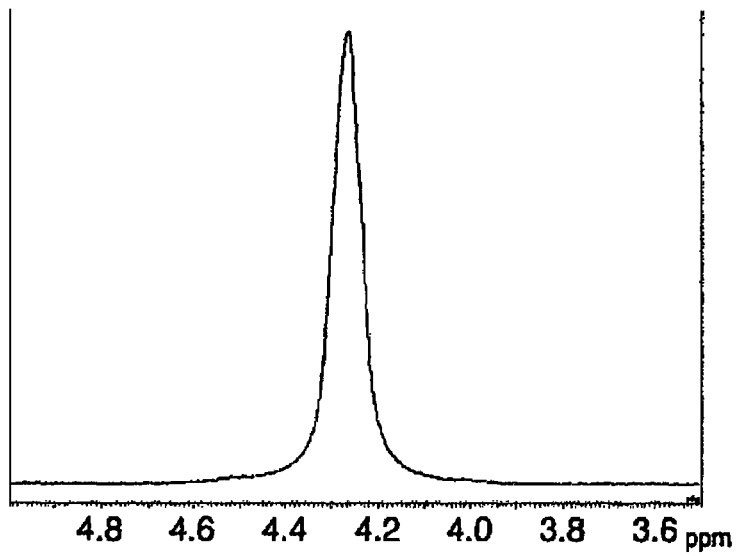
FIG. 1 is a $^1$H NMR spectrum chart of titanium tetra-n-butoxide and that of the partial hydrolysate of titanium tetra-n-butoxide prepared in Preparation Example 7.
Figure 1:
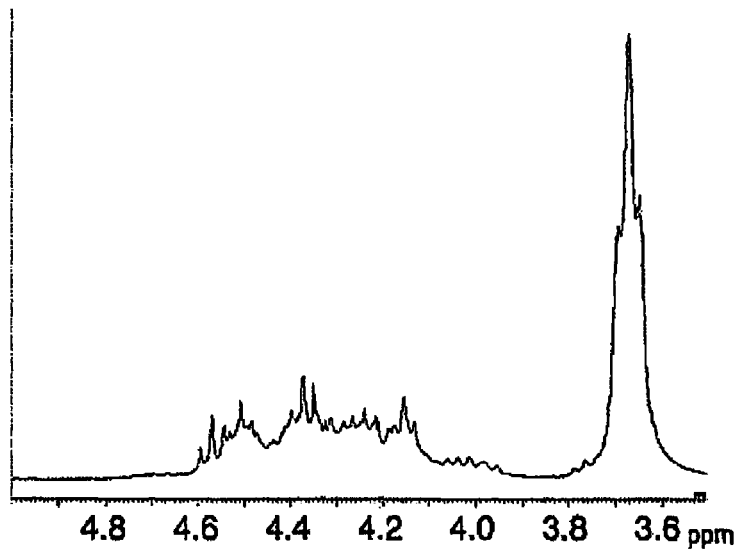
Figure 2:
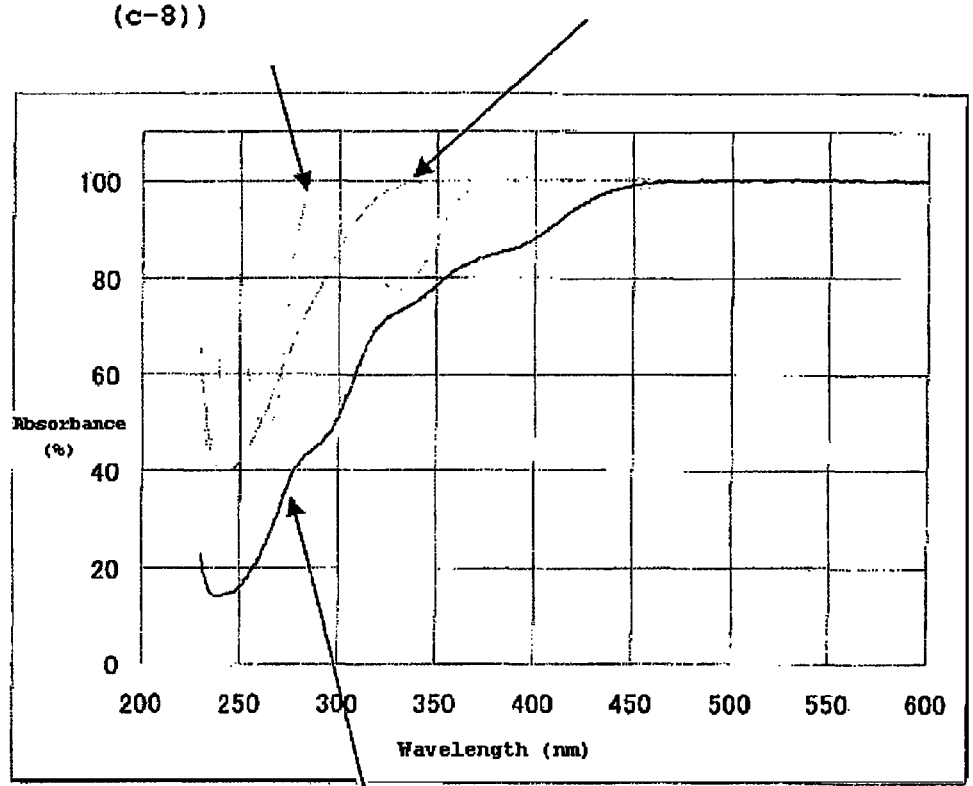
FIG. 2 is data on UV-VIS absorption spectrum of the partial hydrolysate of titanium tetra-n-butoxide prepared in Preparation Example 6, that of (S)-2-(N-3,5-di-tert-butylsalicylidene)amino-3-methyl-1-butanol (above formula (c-8)) and that of the catalyst solution prepared in Example 7.

The invention claimed is:

1. A titanium compound produced from a reaction mixture of a partial hydrolysate of a titanium tetraalkoxide compound and an optically active ligand represented by the general formula (b), or a titanium oxoalkoxide compound represented by the general formula (a) and an optically active ligand represented by the general formula (b), $$[Ti_xO_y](OR^1)_{4x-2y} \quad (a)$$

wherein, in the formula, $R^1$ is an alkyl group or an aryl group, each of which may have a substituent; x is an integer of not less than 2; y is an integer of not less than 1; and y/x satisfies $0.1 < y/x \leq 1.5$,

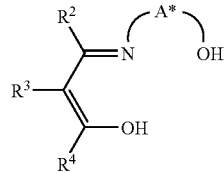

wherein, in the formula, $R^2$, $R^3$ and $R^4$ are independently a hydrogen atom, an alkyl group, an alkenyl group, an aryl group, an aromatic heterocyclic group, an acyl group, an alkoxycarbonyl group or an aryloxycarbonyl group, each of which may have a substituent, two or more of $R^2$, $R^3$ and $R^4$ may be linked together to form a ring, and the ring may have a substituent; and A* represents a hydrocarbon-containing group with three or more carbon atoms having an asymmetric carbon atom or axial asymmetry.

2. The titanium compound as set forth in claim 1, wherein the hydrocarbon-containing group A* in said general formula (b) is a hydrocarbon-containing group represented by any one of the general formulae (A-1), (A-2) or (A-3),

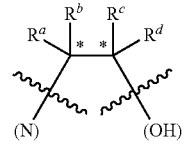

wherein, in the formula, $R^a$, $R^b$, $R^c$ and $R^d$ are each a hydrogen atom, an alkyl group, an aryl group, an alkoxycarbonyl group, an aryloxycarbonyl group or an aminocarbonyl group, each of which may have a substituent, two or more of $R^a$, $R^b$, $R^c$ and $R^d$ may be linked together to form a ring, and the ring may have a substituent; at least one of $R^a$, $R^b$, $R^c$ and $R^d$ is a different group; both or at least one of the carbon atoms indicated as * become an asymmetric center; and parts indicated as (N) and (OH) do not belong to A*, and represent a nitrogen atom and a hydroxyl group corresponding to those in said general formula (b) to which A* is bonded,

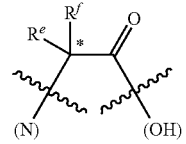

wherein, in the formula, $R^e$ and $R^f$ are each a hydrogen atom, an alkyl group or an aryl group, each of which may have a substituent; $R^e$ and $R^f$ are different substituents and * represents an asymmetric carbon atom; and parts indicated as (N) and (OH) represent the same as those in the general formula (A-1), or

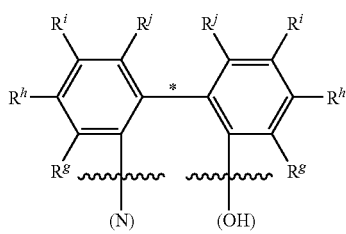
(A-3)

wherein, in the formula, $R^g$, $R^h$, $R^i$ and $R^j$ are independently a hydrogen atom, a halogen atom, an alkyl group, an aryl group or an alkoxy group, each of which may have a substituent, $R^i$ and $R^j$ on the same benzene ring may be linked or condensed together to form a ring, and *' represents an axial asymmetry; and parts indicated as (N) and (OH) represent the same as those in the general formula (A-1).

3. The titanium compound as set forth in claim 1, wherein the optically active ligand represented by said general formula (b) is the following general formula (c),

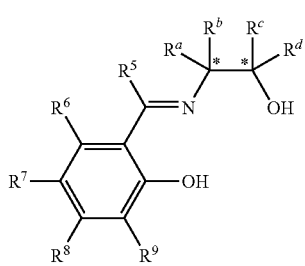
(c)

wherein, in the formula, $R^a$, $R^b$, $R^c$, $R^d$ are each a hydrogen atom, an alkyl group, an aryl group, an alkoxycarbonyl group, an aryloxycarbonyl group or an aminocarbonyl group, each of which may have a substituent, two or more of $R^a$, $R^b$, $R^c$ and $R^d$ may be linked together to form a ring, and the ring may have a substituent; at least one of $R^a$, $R^b$, $R^c$ and $R^d$ is a different group; both or at least one of the carbon atoms indicated as * become an asymmetric center; and parts indicated as (N) and (OH) do not belong to A*, and represent a nitrogen atom and a hydroxyl group corresponding to those in said general formula (b) to which A* is bonded; $R^5$ is a hydrogen atom or an alkyl group, each of which may have a substituent; and $R^6$, $R^7$, $R^8$ and $R^9$ are independently a hydrogen atom, a halogen atom, an alkyl group, an alkenyl group, an aryl group, an aromatic heterocyclic group, a non-aromatic heterocyclic group, an alkoxycarbonyl group, an aryloxycarbonyl group, a hydroxyl group, an alkoxy group, an aryloxy group, an amino group, a cyano group, a nitro group, a silyl group or a siloxy group which may have a substituent, each of which may be linked together to form a ring.

4. A process for producing optically active cyanohydrins, which comprises reacting aldehyde or unsymmetrical ketone with a cyanating agent in the presence of a titanium compound produced from a partial hydrolysate of a titanium tetraalkoxide compound and an optically active ligand represented by the general formula (b), or a titanium oxoalkoxide compound represented by the general formula (a) and an optically active ligand represented by the general formula (b),

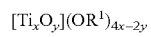
(a)

wherein, in the formula, $R^1$ is an alkyl group or an aryl group, each of which may have a substituent; x is an integer of not less than 2; y is an integer of not less than 1; and y/x satisfies $0.1<y/x<1.5$,

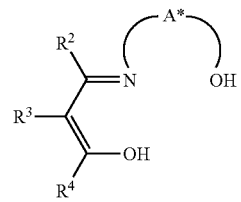
(b)

wherein, in the formula, $R^2$, $R^3$ and $R^4$ are independently a hydrogen atom, an alkyl group, an alkenyl group, an aryl group, an aromatic heterocyclic group, an acyl group, an alkoxycarbonyl group or an aryloxycarbonyl group, each of which may have a substituent, two or more of $R^2$, $R^3$ and $R^4$ may be linked together to form a ring, and the ring may have a substituent; and A* represents a hydrocarbon-containing group with three or more carbon atoms having an asymmetric carbon atom or axial asymmetry.

5. The process for producing optically active cyanohydrins as set forth in claim 4, in which the hydrocarbon-containing group A* in said general formula (b) is a hydrocarbon-containing group represented by any one of the general formulae (A-1), (A-2) or (A-3),

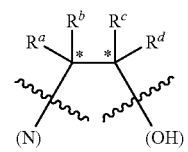
(A-1)

wherein, in the formula, $R^a$, $R^b$, $R^c$ and $R^d$ are each a hydrogen atom, an alkyl group, an aryl group, an alkoxycarbonyl group, an aryloxycarbonyl group or an aminocarbonyl group, each of which may have a substituent, two or more of $R^a$, $R^b$, $R^c$ and $R^d$ may be linked together to form a ring, and the ring may have a substituent; at least one of $R^a$, $R^b$, $R^c$ and $R^d$ is a different group; both or at least one of the carbon atoms indicated as * become an asymmetric center; and parts indicated as (N) and (OH) do not belong to A*, and represent a nitrogen atom and a hydroxyl group corresponding to those in said general formula (b) to which A* is bonded,

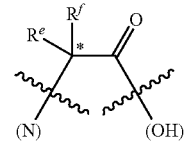
(A-2)

wherein, in the formula, $R^e$ and $R^f$ are each a hydrogen atom, an alkyl group or an aryl group, each of which may have a substituent; $R^e$ and $R^f$ are different substituents and * represents an asymmetric carbon atom; and parts indicated as (N) and (OH) represent the same as those in the general formula (A-1), or

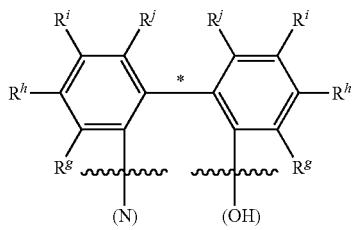

(A-3)

wherein, in the formula, $R^g$, $R^h$, $R^i$ and $R^j$ are independently a hydrogen atom, a halogen atom, an alkyl group, an aryl group or an alkoxy group, each of which may have a substituent, $R^i$ and on the same benzene ring may be linked or condensed together to form a ring, and *' represents an axial asymmetry; and parts indicated as (N) and (OH) represent the same as those in the general formula (A-1).

6. The process for producing optically active cyanohydrins as set forth in claim 4, in which the optically active ligand represented by said general formula (b) is the following general formula (c),

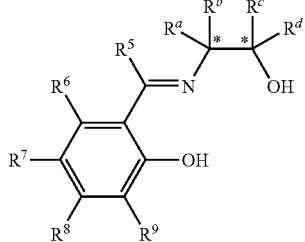

(c)

wherein, in the formula, $R^a$, $R^b$, $R^c$ and $R^d$ represent the same as those in said general formula (A-1); $R^5$ is a hydrogen atom or an alkyl group, each of which may have a substituent;

and $R^6$, $R^7$, $R^8$ and $R^9$ are independently a hydrogen atom, a halogen atom, an alkyl group, an alkenyl group, an aryl group, an aromatic heterocyclic group, a non-aromatic heterocyclic group, an alkoxycarbonyl group, an aryloxycarbonyl group, a hydroxyl group, an alkoxy group, an aryloxy group, an amino group, a cyano group, a nitro group, a silyl group or a siloxy group which may have a substituent, each of which may be linked together to form a ring.

7. The process for producing optically active cyanohydrins as set forth in claim 4, in which said aldehyde or said unsymmetrical ketone is represented by the general formula (d),

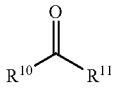

(d)

wherein, in the formula, $R^{10}$ and $R^{11}$ are different groups, and each represent a hydrogen atom, an alkyl group, an alkenyl group, an alkynyl group, an aryl group, an aromatic heterocyclic group or a non-aromatic heterocyclic group, each of which may have a substituent; and $R^{10}$ and $R^{11}$ may be linked together to form a ring.

8. The titanium compound as set forth in claim 1, wherein said titanium tetraalkoxide compound is represented by the general formula (a'),

$Ti(OR^1)_4$ (a')

wherein, in the formula, $R^1$ is an alkyl group or an aryl group, each of which may have a substituent.

9. The process for producing optically active cyanohydrins as set forth in claim 4, in which said titanium tetraalkoxide compound is represented by the general formula (a'),

$Ti(OR^1)_4$ (a')

wherein, in the formula, $R^1$ is an alkyl group or an aryl group, each of which may have a substituent.

10. The process for producing optically active cyanohydrins as set forth in claim 5, in which said aldehyde or said unsymmetrical ketone is represented by the general formula (d),

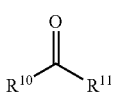

(d)

wherein, in the formula, $R^{10}$ and $R^{11}$ are different groups, and each represent a hydrogen atom, an alkyl group, an alkenyl group, an alkynyl group, an aryl group, an aromatic heterocyclic group or a non-aromatic heterocyclic group, each of which may have a substituent; and $R^{10}$ and $R^{11}$ may be linked together to form a ring.

11. The process for producing optically active cyanohydrins as set forth in claim 6, in which said aldehyde or said unsymmetrical ketone is represented by the general formula (d),

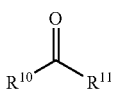

(d)

wherein, in the formula, $R^{10}$ and $R^{11}$ are different groups, and each represent a hydrogen atom, an alkyl group, an alkenyl group, an alkynyl group, an aryl group, an aromatic heterocyclic group or a non-aromatic heterocyclic group, each of which may have a substituent; and $R^{10}$ and $R^{11}$ may be linked together to form a ring.

12. The titanium compound as set forth in claim 2, wherein said titanium tetraalkoxide compound is represented by the general formula (a'),

$Ti(OR^1)_4$ (a')

wherein, in the formula, $R^1$ is an alkyl group or an aryl group, each of which may have a substituent.

13. The titanium compound as set forth in claim 3, wherein said titanium tetraalkoxide compound is represented by the general formula (a'), $$Ti(OR^1)_4 \qquad (a')$$

wherein, in the formula, $R^1$ is an alkyl group or an aryl group, each of which may have a substituent.

14. The process for producing optically active cyanohydrins as set forth in claim 5, in which said titanium tetraalkoxide compound is represented by the general formula (a'), $$Ti(OR^1)_4 \qquad (a')$$

wherein, in the formula, $R^1$ is an alkyl group or an aryl group, each of which may have a substituent.

15. The process for producing optically active cyanohydrins as set forth in claim 6, in which said titanium tetraalkoxide compound is represented by the general formula (a'), $$Ti(OR^1)_4 \qquad (a')$$

wherein, in the formula, $R^1$ is an alkyl group or an aryl group, each of which may have a substituent.

* * * * *